United States Patent
He et al.

(10) Patent No.: US 9,938,355 B2
(45) Date of Patent: Apr. 10, 2018

(54) ANTIBODIES TO ARGININOSUCCINATE SYNTHASE AND RELATED METHODS

(71) Applicant: TDW Group, Grand Cayman (KY)

(72) Inventors: Wei He, San Diego, CA (US); Yunyun Guo, Shanghai (CN); Bor-Wen Wu, San Diego, CA (US)

(73) Assignee: TDW Group, Grand Cayman (KY)

( * ) Notice: Subject to any disclaimer, the term of this patent is extended or adjusted under 35 U.S.C. 154(b) by 62 days.

(21) Appl. No.: 14/794,273

(22) Filed: Jul. 8, 2015

(65) Prior Publication Data

US 2016/0009821 A1    Jan. 14, 2016

Related U.S. Application Data

(60) Provisional application No. 62/022,066, filed on Jul. 8, 2014.

(51) Int. Cl.
| | | |
|---|---|---|
| *G01N 33/573* | (2006.01) | |
| *C07K 16/40* | (2006.01) | |
| *A61K 38/50* | (2006.01) | |
| *C12N 9/78* | (2006.01) | |
| *G01N 33/574* | (2006.01) | |
| *A61K 38/45* | (2006.01) | |
| *A61K 38/51* | (2006.01) | |

(52) U.S. Cl.
CPC .............. *C07K 16/40* (2013.01); *A61K 38/45* (2013.01); *A61K 38/50* (2013.01); *A61K 38/51* (2013.01); *C12N 9/78* (2013.01); *C12Y 207/00* (2013.01); *C12Y 207/03003* (2013.01); *C12Y 401/01019* (2013.01); *G01N 33/573* (2013.01); *G01N 33/57496* (2013.01); *C07K 2317/20* (2013.01); *C07K 2317/565* (2013.01); *C07K 2317/76* (2013.01); *C12Y 305/03006* (2013.01); *G01N 2333/9015* (2013.01); *G01N 2800/52* (2013.01)

(58) Field of Classification Search
CPC combination set(s) only.
See application file for complete search history.

(56) References Cited

U.S. PATENT DOCUMENTS

| 7,323,167 B2 | 1/2008 | Clark |
| 8,663,967 B2 | 3/2014 | Huang et al. |
| 2004/0198959 A1 | 10/2004 | Komatsu et al. |
| 2005/0063942 A1* | 3/2005 | Clark ................ C12Q 1/6883 424/85.1 |
| 2007/0202552 A1 | 8/2007 | Sidhu et al. |
| 2009/0104215 A1 | 4/2009 | Ekiel et al. |
| 2013/0224190 A1 | 8/2013 | Vermot-Desroches et al. |
| 2014/0178351 A1 | 6/2014 | Svetlov et al. |
| 2014/0348814 A1 | 11/2014 | Almassy et al. |

FOREIGN PATENT DOCUMENTS

| WO | WO 2002/063048 A2 | 8/2002 |
| WO | WO 2010/051533 A2 | 5/2010 |
| WO | WO 2013/151568 A1 | 10/2013 |
| WO | WO 2016/007625 A1 | 1/2016 |

OTHER PUBLICATIONS

Raybiotech Antibody 2007;(retrieved from URL: http://www.raybiotech.com/Human-ASS1-monoclonal-antibody-100-ug.html on Apr. 28, 2017).*
Abcam Antibody 2B10 (1998;retrieved from URL://www.abcam.com/ass1-antibody-2b10-ab124465.html on Apr. 28, 2017).*
Jungbluth et al. (Mod Pathol. 2010;23 (Suppl 1:387A. Poster 1727).*
International Application No. PCT/US2015/039553, International Preliminary Report on Patentability dated Jan. 10, 2017, 6 pages.
International Application No. PCT/US2015/039553, International Search Report and Written Opinion dated Oct. 15, 2015, 9 pages.
Ott, P.A. et al., "Phase I/II study of pegylated arginine deiminase (ADI-PEG 20) in patients with advanced melanoma", Invest New Drugs (2013); 31(2): 425-434.
Sugimara, K., et al. "High sensitivity of human melanoma cell lines to the growth inhibitory activity of mycoplasmal arginine deiminase in vitro." Melanoma Research (1992); 2.3: 191-196.
Takaku, Haruo, et al. "Anti-tumor Activity of Arginine Deiminase from Mycoplasma arginini and Its Growth-inhibitory Mechanism." Jpn. J. Cancer Res. (1995); 86.9: 840-846.
European Application No. EP 15819121.3, Extended European Search Report dated Jan. 5, 2018, 9 pages.
Dillon, et al., "Incidence and distribution of argininosuccinate synthetase deficiency in human cancers." Cancer (2004); 100(4): 826-833.

* cited by examiner

*Primary Examiner* — Tracy Vivlemore
*Assistant Examiner* — Carmencita M Belei
(74) *Attorney, Agent, or Firm* — Cooley LLP

(57) ABSTRACT

Antibodies, and antigen-binding fragments, which specifically bind to argininosuccinate synthase, and related compositions, kits, and methods of use, which are useful as companion diagnostics to identify suitable subjects for arginine deprivation or depletion therapies such as ADI-PEG 20 and other arginine deiminase (ADI) polypeptide-based therapies.

22 Claims, 7 Drawing Sheets

```
6-H6    QIQLVQSGPELKKPGETVKISCKTSGYTFTDYSIHWVKQAPGKGLKWMGWINTETGEPTY  60
6-C5    QIQLVQSGPELKKPGETVKISCKTSGYTFTDYSIHWVKQAPGKGLKWMGWINTETGEPTY  60
6-C1    QIQLVQSGPELKKPGETVKISCKTSGYTFTDYSIHWVKQAPGKGLKWMGWINTETGEPTY  60
6-L7    QIQLVQSGPELKKPGETVKISCKTSGYTFTDYSIHWVKQAPGKGLKWMGWINTETGEPTY  60
6-A5    QIQLVQSGPELKKPGETVKISCKTSGYTFTDYSIHWVKQAPGKGLKWMGWINTETGEPTY  60
6-D6    QIQLVQSGPELKKPGETVKISCKTSGYTFTDYSIHWVKQAPGKGLKWMGWINTETGEPTY  60
        ********* *:******.*****************************************

6-H6    ADDFKGRFALSLETSASTAYLQINNLKNEDTATYFCGSYDSYWGQGTLVTVSS  113
6-C5    ADDFKGRFALSLETSASTAYLQINNLKNEDTATYFCGSYDSYWGQGTLVTVSS  113
6-C1    ADDFKGRFALSLETSASTAYLQINNLKNEDTATYFCGSYDSYWGQGTLVTVSS  113
6-L7    ADDFKGRFALSLETSASTAYLQINNLKNEDTATYFCGSYDSYWGQGTLVTVSS  113
6-A5    ADDFKGRFALSLETSASTAYLQINNLKNEDTATYFCGSYDSYWGQGTLVTVSS  113
6-D6    ADDFKGRFALSLETSASTAYLQINNLKNEDTATYFCGSYDSYWGQGTLVTVSS  113
        ****************************************************
```

FIG. 2A

4-5   DVVMTQTPLSLPVSLGDQASISCRSSQSLENSNGNTYLNWFLQRPGQSPQLLIYRVSNRF 60
7-2   DVVMTQTPLSLPVSLGDQASISCRSSQSLENSNGNTYLNWFLQRPGQSPQLLIYRVSNRF 60
7-8   DVVMTQTPLSLPVSLGDQASISCRSSQSLENSNGNTYLNWFLQRPGQSPQLLIYRVSNRF 60
7-12  DVVMTQTPLSLPVSLGDQASISCRSSQSLENSNGNTYLNWFLQRPGQSPQLLIYRVSNRF 60
7-4   DVVMTQTPLSLPVSLGDQASISCRSSQSLENSNGNTYLNWFLQRPGQSPQLLIYRVSNRF 60

4-5   SGVPDRFSGSGSGTEFTLKISRVEAEDLGVYFCLQVTHFPYTFGGGTKLEIK 112
7-2   SGVPDRFSGSGSGTEFTLKISRVEAEDLGVYFCLQVTHFPYTFGGGTKLEIK 112
7-8   SGVPDRFSGSGSGTEFTLKISRVEAEDLGVYFCLQVTHFPYTFGGGTKLEIK 112
7-12  SGVPDRFSGSGSGTEFTLKISRVEAEDLGVYFCLQVTHFPYTFGGGTKLEIK 112
7-4   SGVPDRFSGSGSGTEFTLKISRVEAEDLGVYFCLQVTHFPYTFGGGTKLEIK 112

ANTIBODIES TO ARGININOSUCCINATE SYNTHASE AND RELATED METHODS

CROSS-REFERENCE TO RELATED APPLICATIONS

This application claims priority under 35 U.S.C. § 119(e) to U.S. Application No. 62/022,066, filed Jul. 8, 2014, which is incorporated by reference in its entirety.

STATEMENT REGARDING THE SEQUENCE LISTING

The Sequence Listing associated with this application is provided in text format in lieu of a paper copy, and is hereby incorporated by reference into the specification. The name of the text file containing the Sequence Listing is TDWG_005_01US_ST25.txt. The text file is about 25 KB, was created on Jul. 6, 2015, and is being submitted electronically via EFS-Web.

BACKGROUND

Technical Field

Embodiments of the present invention include antibodies, and antigen-binding fragments thereof, which specifically bind to argininosuccinate synthase, and related compositions, kits, and methods of use thereof, for instance, as companion diagnostics to identify subjects for arginine deprivation or depletion therapies such as ADI-PEG 20 and other arginine depletion-based therapies.

Description of the Related Art

Arginine is a semi-essential amino acid for humans. Cells that are auxotropic for arginine require arginine uptake from their surroundings. Arginine auxotropes tend to be auxotropic because they lack the ability to produce their own arginine from metabolic precursors via the urea cycle.

Some tumors exhibit auxotrophic behavior with respect to amino acids, particularly with the amino acid L-arginine, because they are deficient in argininosuccinate synthase (ASS), the enzyme responsible for converting L-citrulline into L-argininosuccinate. As such, these tumor types require extracellular sources of L-arginine to synthesize proteins.

Arginine deprivation or depletion-based therapies are being developed to take advantage of this auxotrophic behavior. For instance, arginine deiminase (ADI) therapy, for example, ADI-PEG 20, can reduce physiologic levels of L-arginine and starve the tumor of an essential amino acid leading to tumor death (see, e.g., Ott et al., Invest New Drugs. 31:425-34, 2013). Other examples include the use of L-asparaginase to lower circulating levels of asparagine in the treatment of diseases such as acute lymphoblastic leukemia. Also described is the use of arginine-degrading enzymes, which have proven effective in treating melanoma, hepatoma, and some sarcomas, (see, e.g., Sugimura et al., Melanoma Res. 2:191-6, 1992; Takaku et al., Jpn. J. Cancer Res. 86:840-6, 1995).

However, arginine deprivation may not be effective in all patients. To this end, methods have been developed to identify patients that are best-suited to arginine deprivation or depletion therapy, including the use of argininosuccinate synthase expression as a diagnostic marker (see, e.g., WO 2002/063048; and WO 2013/151568). Thus, there is a need in the art for improved reagents that are capable of detecting argininosuccinate synthase expression in a subject or a relevant tissue sample, and thereby identifying patients for arginine deprivation or depletion therapy.

BRIEF DESCRIPTION OF THE FIGURES

FIG. 2A shows an amino acid alignment of the $V_H$ sequences from six productive sub-clones of the hybridoma antibody clone directed against the protein argininosuccinate synthase: 6-H6 (SEQ ID NO:13), 6-C5 (SEQ ID NO:14), 6-C1 (SEQ ID NO:15), 6-L7 (SEQ ID NO:16), 6-A5 (SEQ ID NO:17), and 6-D6 ID NO:18). FIG. 2B shows an amino acid alignment of the $V_L$ sequences from five productive sub-clones: 4-5 (SEQ ID NO:19), 7-2 (SEQ ID NO:20), 7-8 (SEQ ID NO:21), 7-12 (SEQ ID NO:22), and 7-4 (SEQ ID NO:23).

FIG. 5B, skin; FIG. 5C, liver) by immunohistochemical staining with anti-argininosuccinate synthase monoclonal antibody.

FIG. 6A shows strong, positive staining for argininosuccinate synthase expression, and FIGS. 6B-6C show negative staining for argininosuccinate synthase expression.

BRIEF SUMMARY OF THE INVENTION

Figure 1:
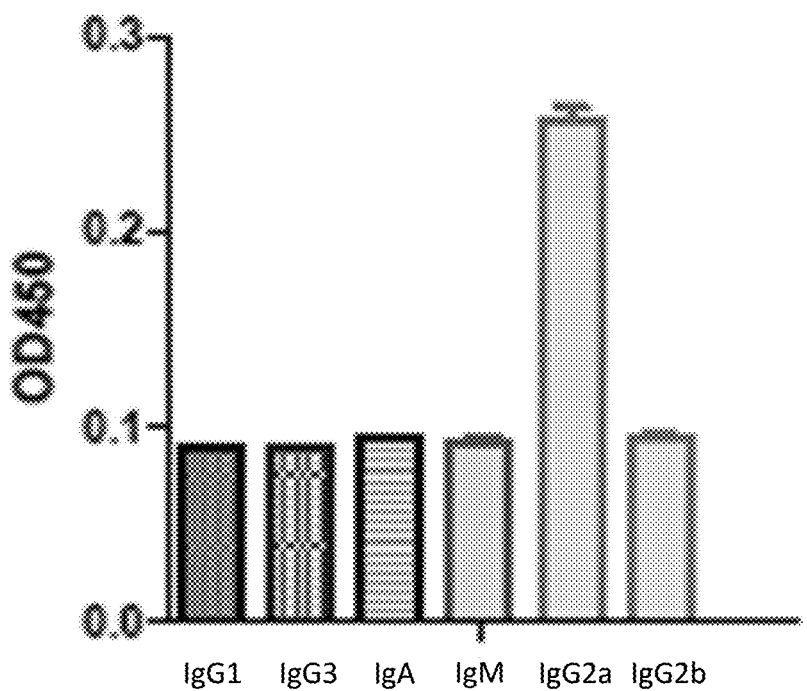
FIG. 1 shows the results of ELISA analysis used to determine the immunoglobulin subtype of a hybridoma antibody clone directed against the protein argininosuccinate synthase.

Embodiments of the present invention include isolated antibodies, or antigen-binding fragments thereof, which specifically bind to a human argininosuccinate synthase polypeptide and (a) comprise a heavy chain variable region ($V_H$) sequence that comprises complementary determining region $V_H$CDR1, $V_H$CDR2, and $V_H$CDR3 sequences set forth respectively in SEQ ID NOs:7, 8, and 9, and a light chain variable region ($V_L$) sequence that comprises complementary determining region $V_L$CDR1, $V_L$CDR2, and $V_L$CDR3 sequences set forth respectively in SEQ ID NOs: 10, 11, and 12; or (b) competitively inhibit the binding of (a) to the human argininosuccinate synthase polypeptide.

In certain embodiments, the $V_H$ sequence is at least 90% identical to SEQ ID NO:1. In certain embodiments, the $V_L$ sequence is at least 90% identical to SEQ ID NO:3. In certain embodiments, the $V_H$ sequence comprises SEQ ID NO:1 and the $V_L$ sequence comprises SEQ ID NO:3.

In certain embodiments, the isolated antibody, or antigen-binding fragment thereof, competitively inhibits the binding of (a) to the human argininosuccinate synthase polypeptide, where (a) is a mouse monoclonal antibody that comprises the $V_H$ sequence set forth in SEQ ID NO:1 and the $V_L$ sequence set forth in SEQ ID NO:3.

In certain embodiments, the isolated antibody, or antigen-binding fragment thereof, competitively inhibits the binding of (a) to the human argininosuccinate synthase polypeptide, where (a) is a mouse monoclonal antibody of subtype IgG1 or IgG2A.

In certain embodiments, the antibody is a whole antibody. In certain embodiments, the antibody is a monoclonal antibody. In certain embodiments, the antibody is selected from of a single chain antibody, a Fab or a Fab' fragment, F(ab')$_2$ fragment, an ScFv, a univalent antibody lacking a hinge region, and a minibody. In certain embodiments, the antibody comprises a mouse or human IgG Fc domain, optionally a IgG1 or IgG2A Fc domain. In certain embodiments, the antibody is a mouse monoclonal antibody of subtype IgG1 or IgG2A.

In certain embodiments, isolated antibody, or antigen-binding fragment thereof, comprises a covalently-attached detectable entity. In certain embodiments, the detectable entity is a fluorophore/fluorescent dye, an iodine-based label, a radioisotope, or a nanoparticle.

Also included are compositions, comprising an antibody, or antigen-binding fragment thereof, described herein, and a suitable carrier.

Certain embodiments relate to methods of determining an amount of human argininosuccinate synthase polypeptide in a biological sample, comprising (a) obtaining or receiving a biological sample, optionally from a subject, (b) contacting the biological sample with an antibody, or antigen-binding fragment thereof, described herein, and (c) measuring the amount of the antibody, or antigen-binding fragment thereof, in the sample, where the amount of the antibody, or antigen-binding fragment thereof, determines the amount of the argininosuccinate synthase polypeptide in the sample.

Also included are methods of identifying a deficiency of argininosuccinate synthase in a biological sample, comprising (a) obtaining or receiving a biological sample, optionally from a subject, (b) contacting the biological sample with an antibody, or antigen-binding fragment thereof, described herein, (b) measuring the amount of the antibody, or antigen-binding fragment thereof, in the sample, where the amount of the antibody, or antigen-binding fragment thereof, determines the amount of argininosuccinate synthase polypeptide in the sample, and (c) identifying a deficiency of argininosuccinate synthase in the sample if the amount of the argininosuccinate synthase polypeptide in the biological sample is reduced relative to a control.

Some embodiments include methods of identifying a subject for arginine deprivation therapy, comprising (a) obtaining or receiving a biological sample from the subject, optionally via a healthcare provider, (b) contacting the biological sample with an antibody, or antigen-binding fragment thereof, described herein, (c) measuring the amount of the antibody, or antigen-binding fragment thereof, in the sample, where the amount of the antibody, or antigen-binding fragment thereof, determine the amount of argininosuccinate synthase polypeptide in the sample, and (d) identifying the subject as suitable for arginine deprivation therapy if the amount of the argininosuccinate synthase polypeptide in the biological sample is reduced relative to a control.

In certain embodiments, step (a) comprises receiving the biological sample from a healthcare provider, and step (d) comprises providing information to the same or different healthcare provider on the amount of the argininosuccinate synthase polypeptide in the biological sample.

Certain embodiment comprise step (e) administering to the subject of (d) at least one arginine depletion agent.

In certain embodiments, the arginine depletion agent is selected from an arginine deiminase (ADI) polypeptide, an arginase polypeptide, an arginine decarboxylase polypeptide, and an arginine kinase polypeptide. In specific embodiments, the ADI polypeptide is ADI-PEG 20.

In particular embodiments, the step (b) comprises performing an immunohistochemistry (IHC) assay.

Also included are methods for diagnosing and treating a subject comprising, (a) analyzing the results of a test that indicates the amount of argininosuccinate synthase polypeptide in a biological sample from the subject, where the test is performed using an antibody, or antigen-binding fragment thereof, described herein, (b) diagnosing the patient as suitable for arginine deprivation therapy if the results from (a) indicate that the amount of argininosuccinate synthase polypeptide in the biological sample is reduced relative to a control, and (c) treating the subject of (b) by administering at least one arginine depletion agent.

Some embodiments include methods for treating a subject, comprising (a) requesting a test that determines the amount of argininosuccinate synthase polypeptide in a biological sample from the subject, where the test is performed using an antibody, or antigen-binding fragment thereof, described herein, (b) and administering to the subject at least one arginine depletion agent if the test from (a) indicates that the amount of argininosuccinate synthase polypeptide in the biological sample is reduced relative to a control.

In certain embodiments, the subject is a human patient. In certain embodiments, the subject has or is suspected of having a cancer. In certain embodiments, the cancer is selected from melanoma, hepatoma optionally hepatocellular carcinoma, pancreatic cancer, prostate cancer, mesothelioma, sarcoma, head and neck cancer, leukemia, acute myeloid leukemia, relapsed acute myeloid leukemia, breast cancer, ovarian cancer, colorectal cancer, gastric cancer, glioma, glioblastoma multiforme, non-small cell lung cancer (NSCLC), kidney cancer, bladder cancer, uterine cancer, esophageal cancer, brain cancer, cervical cancer, testicular cancer, and stomach cancer.

In certain embodiments, the biological sample is a biopsy sample. In certain embodiments, the biopsy sample is a cancer or suspected cancer biopsy sample. In certain embodiments, the biopsy sample is selected from skin tissue, liver tissue, pancreatic tissue, prostate tissue, mesothelial tissue, epithelial tissue, ovarian tissue, colorectal tissue, gastric tissue, brain tissue, lung tissue, kidney tissue, bladder tissue, uterine tissue, esophogeal tissue, cervical tissue, testicular tissue, breast tissue, and mesenchymal tissue such as bone tissue, cartilage tissue, fat tissue, muscle tissue, vascular tissue, blood, or hematopoietic cells/tissue.

In certain embodiments, the control is a reference standard, a biological sample from a healthy subject, or a healthy biological sample from the same subject. In certain embodiments, the control is a non-cancerous biological sample from the same subject, optionally of the same tissue type.

In certain embodiments, the amount of argininosuccinate synthase polypeptide in the biological sample is reduced relative to the control by a statistically significant amount.

In certain embodiments, the amount of argininosuccinate synthase polypeptide in the biological sample is reduced relative to the control by about or at least about 10%, 20%, 30%, 40%, 50%, 60%, 70%, 80%, 90%, or 100%. In certain embodiments, the amount of argininosuccinate synthase polypeptide in the biological sample is undetectable or substantially undetectable.

In certain embodiments, the arginine depletion agent is selected from an arginine deiminase (ADI) polypeptide, an arginase polypeptide, an arginine decarboxylase polypeptide, and an arginine kinase polypeptide. In certain embodiments, the ADI polypeptide is ADI-PEG 20.

Some embodiments include methods for diagnosing and treating a cancer in a human patient comprising, (a) analyzing the results of a test that indicates the amount of argininosuccinate synthase polypeptide in a tumor biopsy from the subject, where the test is performed using an antibody, or antigen-binding fragment thereof, described herein, (b) diagnosing the patient as suitable for ADI-PEG 20 therapy if the results from (a) indicate that the amount of argininosuccinate synthase polypeptide in the tumor biopsy is reduced relative to a control, and (c) treating the subject of (b) by administering ADI-PEG 20.

Also included are methods for treating a cancer in a subject, comprising (a) requesting a test that determines the amount of argininosuccinate synthase polypeptide in a tumor biopsy from the subject, where the test is performed using an antibody, or antigen-binding fragment thereof, described herein, (b) and administering to the subject ADI-PEG 20 if the test from (a) indicates that the amount of argininosuccinate synthase polypeptide in the biological sample is reduced relative to a control.

In certain embodiments, the cancer is selected from melanoma and hepatocellular carcinoma.

In particular embodiments, step (a) comprises analyzing the slides, images, or other results from an immunohistochemistry (IHC) assay.

Some embodiments include one or more kits, comprising an isolated antibody, or antigen-binding fragment thereof, or a composition described herein. Certain kits include instructions for using the antibody according to a method described herein. Some kits further comprise materials for an enzyme-linked immunosorbent assay (ELISA), for example, where the antibody is attached to a solid substrate for performing an ELISA. Certain kits comprise materials for immunohistochemistry (IHC) assays.

Some kits include instructions for using the antibody to identify a subject for arginine deprivation therapy. In certain embodiments, the arginine deprivation therapy is an arginine depletion agent, optionally ADI-PEG 20. Certain kits further comprise at least one arginine depletion agent. In certain embodiments, the arginine depletion agent is selected from an arginine deiminase (ADI) polypeptide, an arginase polypeptide, an arginine decarboxylase polypeptide, and an arginine kinase polypeptide. In certain embodiments, the ADI polypeptide is ADI-PEG 20.

DETAILED DESCRIPTION

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred methods and materials are described. For the purposes of the present invention, the following terms are defined below. All of the patent and non-patent literature references listed herein are incorporated by reference in their entireties.

The articles "a" and "an" are used herein to refer to one or to more than one (i.e., to at least one) of the grammatical object of the article. By way of example, "an element" means one element or more than one element.

By "about" is meant a quantity, level, value, number, frequency, percentage, dimension, size, amount, weight or length that varies by as much as 30, 25, 20, 15, 10, 9, 8, 7, 6, 5, 4, 3, 2 or 1% to a reference quantity, level, value, number, frequency, percentage, dimension, size, amount, weight or length.

As used herein, the term "amino acid" is intended to mean both naturally occurring and non-naturally occurring amino acids as well as amino acid analogs and mimetics. Naturally occurring amino acids include the 20 (L)-amino acids utilized during protein biosynthesis as well as others such as 4-hydroxyproline, hydroxylysine, desmosine, isodesmosine, homocysteine, citrulline and ornithine, for example. Non-naturally occurring amino acids include, for example, (D)-amino acids, norleucine, norvaline, p-fluorophenylalanine, ethionine and the like, which are known to a person skilled in the art. Amino acid analogs include modified forms of naturally and non-naturally occurring amino acids. Such modifications can include, for example, substitution or replacement of chemical groups and moieties on the amino acid or by derivatization of the amino acid. Amino acid mimetics include, for example, organic structures which exhibit functionally similar properties such as charge and charge spacing characteristic of the reference amino acid. For example, an organic structure which mimics Arginine (Arg or R) would have a positive charge moiety located in similar molecular space and having the same degree of mobility as the ε-amino group of the side chain of the naturally occurring Arg amino acid. Mimetics also include constrained structures so as to maintain optimal spacing and charge interactions of the amino acid or of the amino acid functional groups. Those skilled in the art know or can determine what structures constitute functionally equivalent amino acid analogs and amino acid mimetics.

Throughout this specification, unless the context requires otherwise, the words "comprise," "comprises," and "comprising" will be understood to imply the inclusion of a stated step or element or group of steps or elements but not the exclusion of any other step or element or group of steps or elements. By "consisting of" is meant including, and limited to, whatever follows the phrase "consisting of." Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they materially affect the activity or action of the listed elements.

The term "biological sample" includes a biological material that can be collected from a subject and used in connection with diagnosis or monitoring of biological states. Biological samples can include clinical samples, including body fluid samples, such as body cavity fluids, urinary fluids, cerebrospinal fluids, blood, and other liquid samples of biological origin; and tissue samples, such as biopsy samples, tumor or suspected tumor samples, and other solid samples of biological origin. Biological samples can also include those that are manipulated in some way after their collection, such as by treatment with reagents, culturing, solubilization, enrichment for certain biological constituents, cultures or cells derived therefrom, and the progeny thereof.

The term "conjugate" includes an entity formed as a result of covalent or non-covalent attachment or linkage of an agent or other molecule, e.g., a detectable entity, a biologically active molecule, PEG or other polymer, to an antibody described herein.

A "control" such as a "control subject" or "control tissue" includes a healthy subject or a healthy tissue sample, for example, which is not pathological or diseased. In certain embodiments, a control includes a non-diseased (e.g., non-cancerous) tissue from a different, healthy subject or the same subject being tested or diagnosed. A control can also include a reference standard, for example, a standard value generated from one or more healthy subjects or tissues.

As used herein, the terms "function" and "functional" and the like refer to a biological, enzymatic, or therapeutic function.

"Homology" refers to the percentage number of amino acids that are identical or constitute conservative substitutions. Homology may be determined using sequence comparison programs such as GAP (Deveraux et al., Nucleic Acids Research. 12, 387-395, 1984), which is incorporated herein by reference. In this way sequences of a similar or substantially different length to those cited herein could be compared by insertion of gaps into the alignment, such gaps being determined, for example, by the comparison algorithm used by GAP.

By "isolated" is meant material that is substantially or essentially free from components that normally accompany it in its native state. For example, an "isolated peptide" or an "isolated polypeptide" and the like, as used herein, includes the in vitro isolation and/or purification of a peptide or polypeptide molecule from its natural cellular environment, and from association with other components of the cell; i.e., it is not significantly associated with in vivo substances. In particular embodiments, the isolated polypeptide is an antibody.

A "decreased" or "reduced" amount is typically a "statistically significant" amount, and may include, for example, a 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100% decrease (including all integers and ranges in between) relative to a control. Other examples of comparisons and "statistically significant" amounts are described herein.

In certain embodiments, the "purity" of any given agent (e.g., an antibody) in a composition may be specifically defined. For instance, certain compositions may comprise an agent that is at least 80%, 85%, 90%, 91%, 92%, 93%, 94%, 95%, 96%, 97%, 98%, 99%, or 100% pure, including all decimals in between, as measured, for example and by no means limiting, by high performance liquid chromatography (HPLC), a well-known form of column chromatography used frequently in biochemistry and analytical chemistry to separate, identify, and quantify compounds.

The terms "polypeptide" and "protein" are used interchangeably herein to refer to a polymer of amino acid residues and to variants and synthetic analogues of the same. Thus, these terms apply to amino acid polymers in which one or more amino acid residues are synthetic non-naturally occurring amino acids, such as a chemical analogue of a corresponding naturally occurring amino acid, as well as to naturally-occurring amino acid polymers. The polypeptides described herein are not limited to a specific length of the product; thus, peptides, oligopeptides, and proteins are included within the definition of polypeptide, and such terms may be used interchangeably herein unless specifically indicated otherwise. The polypeptides described herein may also comprise post-expression modifications, such as glycosylations, acetylations, phosphorylations and the like, as well as other modifications known in the art, both naturally occurring and non-naturally occurring. A polypeptide may be an entire protein, or a subsequence, fragment, variant, or derivative thereof.

The term "reference sequence" refers generally to a nucleic acid coding sequence, or amino acid sequence, to which another sequence is being compared. All polypeptide and polynucleotide sequences described herein are included as references sequences, including those described by name and those described in the Tables and the Sequence Listing.

The terms "sequence identity" or, for example, comprising a "sequence 50% identical to," as used herein, refer to the extent that sequences are identical on a nucleotide-by-nucleotide basis or an amino acid-by-amino acid basis over a window of comparison. Thus, a "percentage of sequence identity" may be calculated by comparing two optimally aligned sequences over the window of comparison, determining the number of positions at which the identical nucleic acid base (e.g., A, T, C, G, I) or the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity. Included are nucleotides and polypeptides having at least about 50%, 55%, 60%, 65%, 70%, 75%, 80%, 85%, 90%, 95%, 97%, 98%, 99% or 100% sequence identity to any of the reference sequences described herein (see, e.g., Sequence Listing), typically where the polypeptide variant maintains at least one biological activity of the reference polypeptide.

Terms used to describe sequence relationships between two or more polynucleotides or polypeptides include "reference sequence," "comparison window," "sequence identity," "percentage of sequence identity," and "substantial identity." A "reference sequence" is at least 12 but frequently 15 to 18 and often at least 25 monomer units, inclusive of nucleotides and amino acid residues, in length. Because two polynucleotides may each comprise (1) a sequence (i.e., only a portion of the complete polynucleotide sequence) that is similar between the two polynucleotides, and (2) a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window" refers to a conceptual segment of at least 6 contiguous positions, usually about 50 to about 100, more usually about 100 to about 150 in which a sequence is compared to a reference sequence of the same number of contiguous positions after the two sequences are optimally aligned. The comparison window may comprise additions or deletions (i.e., gaps) of about 20% or less as compared to the reference sequence (which does not comprise additions or deletions) for optimal alignment of the two sequences. Optimal alignment of sequences for aligning a comparison window may be conducted by computerized implementations of algorithms (GAP, BESTFIT, FAST A, and TFASTA in the Wisconsin Genetics Software Package Release 7.0, Genetics Computer Group, 575 Science Drive Madison, Wis., USA) or by inspection and the best alignment (i.e., resulting in the highest percentage homology over the comparison window) generated by any of the various methods selected. Reference also may be made to the BLAST family of programs as for example disclosed by Altschul et al., Nucl. Acids Res. 25:3389, 1997. A detailed discussion of sequence analysis can be found in Unit 19.3 of Ausubel et al., "Current Protocols in Molecular Biology," John Wiley & Sons Inc., 1994-1998, Chapter 15.

By "statistically significant," it is meant that the result was unlikely to have occurred by chance. Statistical significance can be determined by any method known in the art. Commonly used measures of significance include the p-value, which is the frequency or probability with which the observed event would occur, if the null hypothesis were true. If the obtained p-value is smaller than the significance level, then the null hypothesis is rejected. In simple cases, the significance level is defined at a p-value of 0.05 or less.

The term "solubility" refers to the property of an antibody described herein to dissolve in a liquid solvent and form a homogeneous solution. Solubility is typically expressed as a concentration, either by mass of solute per unit volume of solvent (g of solute per kg of solvent, g per dL (100 mL), mg/mL, etc.), molarity, molality, mole fraction or other similar descriptions of concentration. The maximum equilibrium amount of solute that can dissolve per amount of solvent is the solubility of that solute in that solvent under the specified conditions, including temperature, pressure, pH, and the nature of the solvent. In certain embodiments, solubility is measured at physiological pH, or other pH, for example, at pH 5.0, pH 6.0, pH 7.0, or pH 7.4. In certain embodiments, solubility is measured in water or a physiological buffer such as PBS or NaCl (with or without NaP). In specific embodiments, solubility is measured at relatively lower pH (e.g., pH 6.0) and relatively higher salt (e.g., 500 mM NaCl and 10 mM NaP). In certain embodiments, solubility is measured in a biological fluid (solvent) such as blood or serum. In certain embodiments, the temperature can be about room temperature (e.g., about 20, 21, 23, 24, 25° C.) or about body temperature (~37° C.). In certain embodiments, an antibody has a solubility of at least about 0.1, 0.2, 0.3, 0.4, 0.5, 0.6, 0.7, 0.8, 0.9, 1, 2, 3, 4, 5, 6, 7, 8, 9, 10, 11, 12, 13, 14, 16, 17, 18, 19, 20, 25, or 30 mg/mL at room temperature or at about 37° C.

A "subject," as used herein, includes any animal that exhibits a symptom or condition, or is at risk for or suspected of exhibiting a symptom or condition, which can be diagnosed with an antibody described herein. Suitable subjects (patients) include laboratory animals (such as mouse, rat, rabbit, or guinea pig), farm animals, and domestic animals or pets (such as a cat or dog). Non-human primates and, preferably, human patients, are included.

A "subject subpopulation" or "patient subpopulation," as used herein, includes a subject or patient subset characterized as having one or more distinctive measurable and/or identifiable characteristics that distinguishes the subject or patient subset from others in the broader disease category (e.g., cancer) to which it belongs. Such characteristics include disease subcategories, gender, lifestyle, health history, organs/tissues involved, treatment history, etc. In some embodiments, a patient or subject subpopulation is characterized by the (e.g., reduced) amount or levels of argininosuccinate synthase polypeptide in a biological sample, for example, a tumor sample.

"Substantially" or "essentially" means nearly totally or completely, for instance, 95%, 96%, 97%, 98%, 99% or greater of some given quantity.

"Substantially free" refers to the nearly complete or complete absence of a given quantity for instance, less than about 10%, 5%, 4%, 3%, 2%, 1%, 0.5% or less of some given quantity. For example, certain compositions may be "substantially free" of cell proteins, membranes, nucleic acids, endotoxins, or other contaminants.

"Treatment" or "treating," as used herein, includes any desirable effect on the symptoms or pathology of a disease or condition, and may include even minimal changes or improvements in one or more measurable markers of the disease or condition being treated. "Treatment" or "treating" does not necessarily indicate complete eradication or cure of the disease or condition, or associated symptoms thereof. The subject receiving this treatment is any subject in need thereof. Exemplary markers of clinical improvement will be apparent to persons skilled in the art.

The term "wild-type" refers to a gene or gene product that has the characteristics of that gene or gene product when isolated from a naturally-occurring source. A wild-type gene or gene product (e.g., a polypeptide) is that which is most frequently observed in a population and is thus arbitrarily designed the "normal" or "wild-type" form of the gene.

Antibodies

Certain embodiments relate to antibodies which specifically bind to a human argininosuccinate synthase polypeptide, including those that bind to one or more contiguous or non-contiguous fragments or epitopes thereof. In some embodiments, the antibodies are defined by the light chain variable region sequences and/or heavy chain variable regions described herein, and/or the complementary determining region (CDR) sequences or antigen-binding regions (ABRs) contained therein, including variants and combinations of these sequences that specifically bind to human argininosuccinate synthase. Also included are antibodies that competitively inhibit the binding of such antibodies to human argininosuccinate synthase.

Exemplary antibody sequence are provided in Table 1 below.

TABLE 1

Exemplary Polypeptide Sequences

| Description | Sequence | SEQ ID NO: |
|---|---|---|
| Heavy chain variable region ($V_H$) | QIQLVQSGPELKKPGETVKISCKTSGY TFTDYSIHWVKQAPGKGLTWMGWINTE TGEPTYADDFKGRFALSLETSASTAYL QLKNLRNEDTATYFCGSSYSYWGQGTL VTVSS | 1 |
| Light chain variable region ($V_L$) | DVVMTQTPLSLPVSLGDQASISCRSSQ SLENSNGKTYLNWFLQKPGQSPQLLIY RVSNRFSGVPDRFSGSGSGTEFTLKIS RVEAEDLGVYFCLQVKHVPWTFGGGTK LEIK | 3 |
| $V_H$CDR1 | GYTFTDYS | 7 |
| $V_H$CDR2 | INTETGEP | 8 |
| $V_H$CDR3 | GSSYSY | 9 |
| $V_L$CDR1 | QSLENSNGKTY | 10 |
| $V_L$CDR2 | RVS | 11 |
| $V_L$CDR3 | LQVKHVPWT | 12 |

Hence, in certain embodiments, an antibody, or antigen-binding fragment thereof, comprises one or more of the sequences in Table 1 (e.g., SEQ ID NOs:1, 3, 7-12), including combinations and variants thereof. For instance, in particular embodiments, the antibody, or antigen-binding fragment thereof, comprises the $V_H$ sequence set forth SEQ ID NO:1, and/or the $V_L$ sequence set forth in SEQ ID NO:3. In some embodiments, the antibody, or antigen-binding fragment thereof, comprises a heavy chain variable region ($V_H$) that comprises complementary determining region $V_H$CDR1, $V_H$CDR2, and $V_H$CDR3 sequences contained in SEQ ID NO: 1 (e.g., SEQ ID NOS:7, 8, and 9, respectively), and/or a light chain variable region ($V_L$) that comprises complementary determining region $V_L$CDR1, $V_L$CDR2, and $V_L$CDR3 sequence contained in SEQ ID NO:3 (e.g., SEQ ID NOS:10, 11, and 12, respectively). In some embodiments, the CDR sequences are defined according to the rules of Kabat, Clothia, or combinations thereof (see also IMGT®, the international ImMunoGeneTics information System®).

The term "antigen-binding fragment" as used herein refers to a polypeptide fragment that contains at least one CDR of an immunoglobulin heavy and/or light chains that bind to the antigen of interest. In this regard, an antigen-binding fragment of the herein described antibodies may comprise 1, 3, 4, 5, or all 6 CDRs of a $V_H$ and $V_L$ sequence from antibodies that specifically bind to a therapeutic or diagnostic target such as human argininosuccinate synthase polypeptide including fragments thereof.

The term "antigen" refers to a molecule or a portion of a molecule capable of being bound by a selective antibody, or an antigen-binding fragment thereof, and additionally capable of being used in an animal to produce antibodies capable of binding to an epitope of that antigen. An antigen may have one or more epitopes.

The term "epitope" includes any determinant, preferably a polypeptide determinant, capable of specific binding to an immunoglobulin or T-cell receptor. An epitope is a region of an antigen that is bound by an antibody. In certain embodiments, epitope determinants include chemically active surface groupings of molecules such as amino acids, sugar side chains, phosphoryl or sulfonyl, and may in certain embodiments have specific three-dimensional structural characteristics, and/or specific charge characteristics. Epitopes can be contiguous or non-contiguous in relation to the primary structure of the antigen.

An antibody, antigen-binding fragment thereof, is said to exhibit "specific binding" or "preferential binding" if it reacts or associates more frequently, more rapidly, with greater duration and/or with greater affinity with a particular cell or substance than it does with alternative cells or substances. An antibody "specifically binds" or "preferentially binds" to a target if it binds with greater affinity, avidity, more readily, and/or with greater duration than it binds to other substances. For example, an antibody that specifically or preferentially binds to a specific epitope is an antibody that binds that specific epitope with greater affinity, avidity, more readily, and/or with greater duration than it binds to other epitopes. It is also understood by reading this definition that, for example, an antibody (or moiety or epitope) that specifically or preferentially binds to a first target may or may not specifically or preferentially bind to a second target. As such, "specific binding" or "preferential binding" does not necessarily require (although it can include) exclusive binding. Generally, but not necessarily, reference to binding means preferential binding.

Immunological binding generally refers to the non-covalent interactions of the type which occur between an immunoglobulin molecule and an antigen for which the immunoglobulin is specific, for example by way of illustration and not limitation, as a result of electrostatic, ionic, hydrophilic and/or hydrophobic attractions or repulsion, steric forces, hydrogen bonding, van der Waals forces, and other interactions. The strength, or affinity of immunological binding interactions can be expressed in terms of the dissociation constant ($K_d$) of the interaction, wherein a smaller $K_d$ represents a greater affinity. Immunological binding properties of selected polypeptides can be quantified using methods well known in the art. One such method entails measuring the rates of antigen-binding site/antigen complex formation and dissociation, wherein those rates depend on the concentrations of the complex partners, the affinity of the interaction, and on geometric parameters that equally influence the rate in both directions. Thus, both the "on rate constant" ($k_{on}$) and the "off rate constant" ($k_{off}$) can be determined by calculation of the concentrations and the actual rates of association and dissociation. The ratio of $k_{off}/k_{on}$ enables cancellation of all parameters not related to affinity, and is thus equal to the dissociation constant $K_d$.

Immunological binding properties of antibodies, and antigen-binding fragments thereof, can be quantified using methods well known in the art (see Davies et al., *Annual Rev. Biochem.* 59:439-473, 1990). In some embodiments, an antibody is said to specifically bind an antigen or epitope thereof when the equilibrium dissociation constant is about $\leq 10^{-7}$ or $10^{-8}$ M. In some embodiments, the equilibrium dissociation constant of a protein may be about $\leq 10^{-9}$ M or $\leq 10^{-10}$ M. In certain illustrative embodiments, a protein has an affinity ($K_d$) for an antigen or target described herein (to which it specifically binds) of about, at least about, or no more than about 0.01, 0.05, 0.1, 0.2, 0.3, 0.4, 0.5, 0.6, 0.7, 0.8, 0.9, 1, 2, 3, 4, 6, 7, 8, 9, 10, 11, 12, 13, 14, 15, 16, 17, 18, 19, 20, 21, 22, 23, 24, 25, 26, 27, 28, 29, 30, 40, or 50 nM.

As noted above, the antibodies described herein specifically bind to a human argininosuccinate synthase polypeptide or a fragment or epitope thereof. Argininosuccinate synthase or synthetase (ASS or ASS1) (EC 6.3.4.5) is an enzyme that catalyzes the synthesis of argininosuccinate from citrulline and aspartate. Argininosuccinate synthase is responsible for the third step of the urea cycle and one of the reactions of the citrulline-NO cycle. The primary amino acid sequence of human argininosuccinate synthase is shown in Table 2 below.

TABLE 2

Human argininosuccinate synthase

| Name | Amino acid sequence | SEQ ID NO: |
|---|---|---|
| Human argininosuccinate synthase | MSSKGSVVLAYSGGLDTSCILVWLKEQGY DVIAYLANIGQKEDFEEARKKALKLGAKK VFIEDVSREFVEEFIWPAIQSSALYEDRY LLGTSLARPCIARKQVEIAQREGAKYVSH GATGKGNDQVRFELSCYSLAPQIKVIAPW RMPEFYNRFKGRNDLMEYAKQHGIPIPVT PKNPWSMDENLMHISYEAGILENPKNQAP PGLYTKTQDPAKAPNTPDILEIEFKKGVP VKVTNVKDGTTHQTSLELFMYLNEVAGKH GVGRIDIVENRFIGMKSRGIYETPAGTIL YHAHLDIEAFTMDREVRKIKQGLGLKFAE LVYTGFWHSPECEFVRHCIAKSQERVEGK VQVSVLKGQVYILGRESPLSLYNEELVSM NVQGDYEPTDATGFININSLRLKEYHRLQ SKVTAK | 5 |

Hence, the antibodies described herein specifically bind to a polypeptide of SEQ ID NO:5, or a fragment or epitope thereof. In certain embodiments, such antibodies specifically bind to a contiguous fragment of about or at least about 5, 6, 7, 8, 9, 10, 11, 12, 13, 14, 15, 16, 17, 18, 19, 20, 21, 22, 23, 24, 26, 27, 28, 29, 30, 40, or 50 or more amino acids of SEQ ID NO:5.

In certain embodiments, antibodies and antigen-binding fragments thereof as described herein include a heavy chain and a light chain CDR set, respectively interposed between a heavy chain and a light chain framework region (FR) set which provide support to the CDRs and define the spatial relationship of the CDRs relative to each other. As used herein, the term "CDR set" refers to the three hypervariable regions of a heavy or light chain V region. Proceeding from the N-terminus of a heavy or light chain, these regions are denoted as "CDR1," "CDR2," and "CDR3" respectively. An antigen-binding site, therefore, includes six CDRs, comprising the CDR set from each of a heavy and a light chain V region. A polypeptide comprising a single CDR, (e.g., a CDR1, CDR2 or CDR3) is referred to herein as a "molecular recognition unit." Crystallographic analysis of a number of antigen-antibody complexes has demonstrated that the amino acid residues of CDRs form extensive contact with bound antigen, wherein the most extensive antigen contact is with the heavy chain CDR3. Thus, the molecular recognition units are primarily responsible for the specificity of an antigen-binding site.

As used herein, the term "FR set" refers to the four flanking amino acid sequences which frame the CDRs of a CDR set of a heavy or light chain V region. Some FR residues may contact bound antigen; however, FRs are primarily responsible for folding the V region into the antigen-binding site, particularly the FR residues directly adjacent to the CDRs. Within FRs, certain amino residues and certain structural features are very highly conserved. In this regard, all V region sequences contain an internal disulfide loop of around 90 amino acid residues. When the V regions fold into a binding-site, the CDRs are displayed as projecting loop motifs which form an antigen-binding surface. It is generally recognized that there are conserved structural regions of FRs which influence the folded shape of the CDR loops into certain "canonical" structures-regardless of the precise CDR amino acid sequence. Further, certain FR residues are known to participate in non-covalent interdomain contacts which stabilize the interaction of the antibody heavy and light chains.

The structures and locations of immunoglobulin variable domains may be determined by reference to Kabat, E. A. et al., Sequences of Proteins of Immunological Interest. 4th Edition. US Department of Health and Human Services. 1987, and updates thereof.

In some embodiments, the antibody is a "monoclonal antibody," which refers to a homogeneous antibody population wherein the monoclonal antibody is comprised of amino acids (naturally occurring and non-naturally occurring) that are involved in the selective binding of an epitope. Monoclonal antibodies are highly specific, being directed against a single epitope. The term "monoclonal antibody" encompasses not only intact monoclonal antibodies and full-length monoclonal antibodies, but also fragments thereof (such as Fab, Fab', F(ab')$_2$, Fv), single chain (ScFv), variants thereof, fusion proteins comprising an antigen-binding portion, humanized monoclonal antibodies, chimeric monoclonal antibodies, and any other modified configuration of the immunoglobulin molecule that comprises an antigen-binding fragment (epitope recognition site) of the required specificity and the ability to bind to an epitope. It is not intended to be limited as regards the source of the antibody or the manner in which it is made (e.g., by hybridoma, phage selection, recombinant expression, transgenic animals). The term includes whole immunoglobulins as well as the fragments, etc. described herein under the definition of "antibody."

The proteolytic enzyme papain preferentially cleaves IgG molecules to yield several fragments, two of which (the F(ab) fragments) each comprise a covalent heterodimer that includes an intact antigen-binding site. The enzyme pepsin is able to cleave IgG molecules to provide several fragments, including the F(ab')$_2$ fragment which comprises both antigen-binding sites. An Fv fragment for use according to certain embodiments of the present invention can be produced by preferential proteolytic cleavage of an IgM, and on rare occasions of an IgG or IgA immunoglobulin molecule. Fv fragments are, however, more commonly derived using recombinant techniques known in the art. The Fv fragment includes a non-covalent $V_H::V_L$ heterodimer including an antigen-binding site which retains much of the antigen recognition and binding capabilities of the native antibody molecule. See Inbar et al., *PNAS USA*. 69:2659-2662, 1972; Hochman et al., *Biochem*. 15:2706-2710, 1976; and Ehrlich et al., *Biochem*. 19:4091-4096, 1980.

In certain embodiments, single chain Fv or scFV antibodies are contemplated. For example, Kappa bodies (Ill et al., *Prot. Eng*. 10:949-57, 1997); minibodies (Martin et al., *EMBO J* 13:5305-9, 1994); diabodies (Holliger et al., *PNAS* 90:6444-8, 1993); or Janusins (Traunecker et al., *EMBO J* 10:3655-59, 1991; and Traunecker et al., *Int. J. Cancer Suppl*. 7:51-52, 1992), may be prepared using standard molecular biology techniques following the teachings of the present application with regard to selecting antibodies having the desired specificity.

A single chain Fv (sFv) polypeptide is a covalently linked $V_H::V_L$ heterodimer which is expressed from a gene fusion including $V_H$- and $V_L$-encoding genes linked by a peptide-encoding linker. Huston et al. (*PNAS USA*. 85(16):5879-5883, 1988). A number of methods have been described to discern chemical structures for converting the naturally aggregated—but chemically separated—light and heavy polypeptide chains from an antibody V region into an sFv molecule which will fold into a three dimensional structure substantially similar to the structure of an antigen-binding site. See, e.g., U.S. Pat. Nos. 5,091,513 and 5,132,405, to Huston et al.; and U.S. Pat. No. 4,946,778, to Ladner et al.

In certain embodiments, the antibodies or antigen-binding fragments thereof are humanized. These embodiments refer to a chimeric molecule, generally prepared using recombinant techniques, having an antigen-binding site derived from an immunoglobulin from a non-human species and the remaining immunoglobulin structure of the molecule based upon the structure and/or sequence of a human immunoglobulin. The antigen-binding site may comprise either complete variable domains fused onto constant domains or only the CDRs grafted onto appropriate framework regions in the variable domains. Epitope binding sites may be wild-type or modified by one or more amino acid substitutions. This eliminates the constant region as an immunogen in human individuals, but the possibility of an immune response to the foreign variable region remains (LoBuglio et al., *PNAS USA* 86:4220-4224, 1989; Queen et al., *PNAS USA*. 86:10029-10033, 1988; Riechmann et al., *Nature*. 332:323-327, 1988). Illustrative methods for humanization of antibodies include the methods described in U.S. Pat. No. 7,462,697.

Another approach focuses not only on providing human-derived constant regions, but modifying the variable regions as well so as to reshape them as closely as possible to human form. It is known that the variable regions of both heavy and light chains contain three complementarity-determining regions (CDRs) which vary in response to the epitopes in question and determine binding capability, flanked by four framework regions (FRs) which are relatively conserved in a given species and which putatively provide a scaffolding for the CDRs. When nonhuman antibodies are prepared with respect to a particular epitope, the variable regions can be "reshaped" or "humanized" by grafting CDRs derived from a nonhuman antibody on the FRs present in the human antibody to be modified. Application of this approach to various antibodies has been reported by Sato et al., *Cancer Res.* 53:851-856, 1993; Riechmann et al., *Nature* 332:323-327, 1988; Verhoeyen et al., *Science* 239:1534-1536, 1988; Kettleborough et al., *Protein Engineering.* 4:773-3783, 1991; Maeda et al., *Human Antibodies Hybridoma* 2:124-134, 1991; Gorman et al., *PNAS USA.* 88:4181-4185, 1991; Tempest et al., *Bio/Technology* 9:266-271, 1991; Co et al., *PNAS USA.* 88:2869-2873, 1991; Carter et al., *PNAS USA.* 89:4285-4289, 1992; and Co et al., *J Immunol.* 148:1149-1154, 1992. In some embodiments, humanized antibodies preserve all CDR sequences (for example, a humanized mouse antibody which contains all six CDRs from the mouse antibodies). In other embodiments, humanized antibodies have one or more CDRs (one, two, three, four, five, six) which are altered with respect to the original antibody, which are also termed one or more CDRs "derived from" one or more CDRs from the original antibody.

The antibodies, and antigen-binding fragments thereof, described herein can comprise the light chain constant regions or heavy chain constant regions (e.g., Fc regions) of any variety of immunoglobulin subtypes (e.g., IgA, IgD, IgE, IgG, IgM, including subclasses and combinations thereof, e.g., IgG1, IgG2, IgG3, IgG4), from any variety of mammals such as mouse, human, rabbit, or goat. The "Fc region" sequence is usually derived from the heavy chain of an immunoglobulin (Ig) molecule. A typical Ig molecule is composed of two heavy chains and two light chains. The heavy chains can be divided into at least three functional regions: the Fd region, the Fc region (fragment crystallizable region), and the hinge region, the latter being found only in IgG, IgA, and IgD immunoglobulins. The Fd region comprises the variable (VH) and constant (CH1) domains of the heavy chains, and together with the variable (VL) and constant (CL) domains of the light chains forms the antigen-binding fragment or Fab region.

The Fc region of IgG, IgA, and IgD immunoglobulins comprises the heavy chain constant domains 2 and 3, designated respectively as CH2 and CH3 regions; and the Fc region of IgE and IgM immunoglobulins comprises the heavy chain constant domains 2, 3, and 4, designated respectively as CH2, CH3, and CH4 regions. The Fc region is mainly responsible for the immunoglobulin effector functions, which include, for example, complement fixation and binding to cognate Fc receptors of effector cells.

The hinge region (found in IgG, IgA, and IgD) acts as a flexible spacer that allows the Fab portion to move freely in space relative to the Fc region. In contrast to the constant regions, the hinge regions are structurally diverse, varying in both sequence and length among immunoglobulin classes and subclasses (see supra). The hinge region may also contain one or more glycosylation site(s), which include a number of structurally distinct types of sites for carbohydrate attachment. For example, IgA1 contains five glycosylation sites within a 17 amino acid segment of the hinge region, conferring significant resistance of the hinge region polypeptide to intestinal proteases. Residues in the hinge proximal region of the CH2 domain can also influence the specificity of the interaction between an immunoglobulin and its respective Fc receptor(s) (see, e.g., Shin et al., *Intern. Rev. Immunol.* 10:177-186, 1993).

The term "Fc region" or "Fc fragment" or "Fc" as used herein, thus refers to a portion of an antibody, or antigen-binding fragment thereof, which contains one or more of a CH2 region, a CH3 and/or a CH4 region from one or more selected immunoglobulin(s), including fragments and variants and combinations thereof. An "Fc region" may also include one or more hinge region(s) of the heavy chain constant region of an immunoglobulin. In certain embodiments, the Fc region does not contain one or more of the CH1, CL, VL, and/or VH regions of an immunoglobulin.

The Fc region can comprise the CH2 region, CH3 region, CH4 region, and/or hinge region(s) of any one or more immunoglobulin classes, including but not limited to IgA, IgD, IgE, IgG, IgM, including subclasses and combinations thereof. In some embodiments, the Fc region is from an IgA immunoglobulin (e.g., mouse, human, rabbit, goat), including subclasses IgA1 and/or IgA2. In certain embodiments, the Fc region is from an IgD immunoglobulin (e.g., mouse, human, rabbit, goat). In particular embodiments, the Fc region is from an IgE immunoglobulin (e.g., mouse, human, rabbit, goat). In some embodiments, the Fc region is from an IgG immunoglobulin (e.g., mouse, human, rabbit, goat), including subclasses IgG1, IgG2, IgG3, and/or IgG4. In certain embodiments, the Fc region is from an IgM immunoglobulin (e.g., mouse, human, rabbit, goat).

Also included are antibodies, or antigen-binding fragments thereof, which comprise "variants" of the sequences in Table 1 (e.g., variants of SEQ ID NOS: 1, 3, 7-12). A "variant" sequence, as the term is used herein, refers to a polypeptide or polynucleotide sequence that differs from a reference sequence disclosed herein (e.g., Table 1, SEQ ID NOS: 1, 3, 7-12, by one or more substitutions, deletions (e.g., truncations), additions, and/or insertions. Certain variants thus include fragments of a reference sequence described herein. Variant polypeptides are biologically active, that is, they continue to possess the binding activity of a reference polypeptide. Such variants may result from, for example, genetic polymorphism and/or from human manipulation.

In many instances, a biologically active variant will contain one or more conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged. As described above, modifications may be made in the structure of the polynucleotides and polypeptides of the present invention and still obtain a functional molecule that encodes a variant or derivative polypeptide with desirable characteristics. When it is desired to alter the amino acid sequence of a polypeptide to create an equivalent, or even an improved, variant or portion of a polypeptide of the invention, one skilled in the art will typically change one or more of the codons of the encoding DNA sequence according to Table A below.

TABLE A

| Amino Acids | | | Codons | | | |
|---|---|---|---|---|---|---|
| Alanine | Ala | A | GCA | GCC | GCG | GCU |
| Cysteine | Cys | C | UGC | UGU | | |
| Aspartic acid | Asp | D | GAC | GAU | | |
| Glutamic acid | Glu | E | GAA | GAG | | |

TABLE A-continued

| Amino Acids | | | Codons | | | | |
|---|---|---|---|---|---|---|---|
| Phenylalanine | Phe | F | UUC | UUU | | | |
| Glycine | Gly | G | GGA | GGC | GGG | GGU | |
| Histidine | His | H | CAC | CAU | | | |
| Isoleucine | Ile | I | AUA | AUC | AUU | | |
| Lysine | Lys | K | AAA | AAG | | | |
| Leucine | Leu | L | UUA | UUG | CUA | CUC | CUG | CUU |
| Methionine | Met | M | AUG | | | | |
| Asparagine | Asn | N | AAC | AAU | | | |
| Proline | Pro | P | CCA | CCC | CCG | CCU | |
| Glutamine | Gln | Q | CAA | CAG | | | |
| Arginine | Arg | R | AGA | AGG | CGA | CGC | CGG | CGU |
| Serine | Ser | S | AGC | AGU | UCA | UCC | UCG | UCU |
| Threonine | Thr | T | ACA | ACC | ACG | ACU | |
| Valine | Val | V | GUA | GUC | GUG | GUU | |
| Tryptophan | Trp | W | UGG | | | | |
| Tyrosine | Tyr | Y | UAC | UAU | | | |

For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid sequence substitutions can be made in a protein sequence, and, of course, its underlying DNA coding sequence, and nevertheless obtain a protein with like properties. It is thus contemplated that various changes may be made in the peptide sequences of the disclosed compositions, or corresponding DNA sequences which encode said peptides without appreciable loss of their utility.

In making such changes, the hydropathic index of amino acids may be considered. The importance of the hydropathic amino acid index in conferring interactive biologic function on a protein is generally understood in the art (Kyte & Doolittle, 1982, incorporated herein by reference). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Each amino acid has been assigned a hydropathic index on the basis of its hydrophobicity and charge characteristics (Kyte & Doolittle, 1982). These values are: isoleucine (+4.5); valine (+4.2); leucine (+3.8); phenylalanine (+2.8); cysteine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5). It is known in the art that certain amino acids may be substituted by other amino acids having a similar hydropathic index or score and still result in a protein with similar biological activity, i.e., still obtain a biological functionally equivalent protein. In making such changes, the substitution of amino acids whose hydropathic indices are within ±2 is preferred, those within ±1 are particularly preferred, and those within ±0.5 are even more particularly preferred.

It is also understood in the art that the substitution of like amino acids can be made effectively on the basis of hydrophilicity. U.S. Pat. No. 4,554,101 (specifically incorporated herein by reference in its entirety), states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those within ±1 are particularly preferred, and those within ±0.5 are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include: arginine and lysine; glutamate and aspartate; serine and threonine; glutamine and asparagine; and valine, leucine and isoleucine.

Amino acid substitutions may further be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. Other groups of amino acids that may represent conservative changes include: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his.

A variant may also, or alternatively, contain non-conservative changes. In a preferred embodiment, variant polypeptides differ from a native or reference sequence by substitution, deletion or addition of about or fewer than about 10, 9, 8, 7, 6, 5, 4, 3, 2 amino acids, or even 1 amino acid. Variants may also (or alternatively) be modified by, for example, the deletion or addition of amino acids that have minimal influence on the immunogenicity, secondary structure, enzymatic activity, and/or hydropathic nature of the polypeptide.

In general, variants will display at least about 30%, 40%, 50%, 55%, 60%, 65%, 70%, 75%, 80%, 85%, 90%, 91%, 92%, 93%, 94%, 95%, 96%, 97%, 98%, 99% similarity or sequence identity or sequence homology to a reference polypeptide sequence (e.g., Table 1, SEQ ID NOs:1, 3, 7-12). Moreover, sequences differing from the reference sequences by the addition (e.g., C-terminal addition, N-terminal addition, both), deletion, truncation, insertion, or substitution (e.g., conservative substitution) of about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 33, 34, 35, 36, 37, 38, 39, 40, 41, 42, 43, 44, 45, 46, 47, 48, 49, 50, 55, 60, 65, 70, 75, 80, 85, 90, 95, or 100 amino acids (including all integers and ranges in between) but which retain the properties or activities of a parent or reference polypeptide sequence are contemplated.

In some embodiments, variant polypeptides differ from reference sequence by at least one but by less than 50, 40, 30, 20, 15, 10, 9, 8, 7, 6, 5, 4, 3 or 2 amino acid residue(s). In other embodiments, variant polypeptides differ from a reference sequence by at least 1% but less than 20%, 15%, 10% or 5% of the residues. (If this comparison requires alignment, the sequences should be aligned for maximum similarity. In some instances, "looped" out sequences from deletions or insertions, or mismatches, are considered differences.

Calculations of sequence similarity or sequence identity between sequences (the terms are used interchangeably herein) are performed as follows. To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In certain embodiments, the length of a reference sequence aligned for comparison purposes is at least 30%, preferably at least 40%, more preferably at least 50%, 60%, and even more preferably at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position.

The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch, (*J. Mol. Biol.* 48: 1970) algorithm which has been incorporated into the GAP program in the GCG software package, using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package, using a NWSgapdna.CMP matrix and a gap weight of 40, 50, 60, 70, or 80 and a length weight of 1, 2, 3, 5, or 6. A preferred set of parameters includes a Blossum 62 scoring matrix with a gap penalty of 12, a gap extend penalty of 4, and a frameshift gap penalty of 5.

The percent identity between two amino acid or nucleotide sequences can be determined using the algorithm of E. Meyers and W. Miller (*Cabios.* 4:11-17, 1989) which has been incorporated into the ALIGN program (version 2.0), using a PAM120 weight residue table, a gap length penalty of 12 and a gap penalty of 4.

The nucleic acid and protein sequences described herein can be used as a "query sequence" to perform a search against public databases to, for example, identify other family members or related sequences. Such searches can be performed using the NBLAST and XBLAST programs (version 2.0) of Altschul, et al., (1990, *J. Mol. Biol*, 215: 403-10). BLAST nucleotide searches can be performed with the NBLAST program, score=100, wordlength=12 to obtain nucleotide sequences homologous to nucleic acid molecules of the invention. BLAST protein searches can be performed with the XBLAST program, score=50, wordlength=3 to obtain amino acid sequences homologous to protein molecules of the invention. To obtain gapped alignments for comparison purposes, Gapped BLAST can be utilized as described in Altschul et al., (*Nucleic Acids Res.* 25:3389-3402, 1997). When utilizing BLAST and Gapped BLAST programs, the default parameters of the respective programs (e.g., XBLAST and NBLAST) can be used.

In one embodiment, as noted above, polynucleotides and/or polypeptides can be evaluated using a BLAST alignment tool. A local alignment consists simply of a pair of sequence segments, one from each of the sequences being compared. A modification of Smith-Waterman or Sellers algorithms will find all segment pairs whose scores cannot be improved by extension or trimming, called high-scoring segment pairs (HSPs). The results of the BLAST alignments include statistical measures to indicate the likelihood that the BLAST score can be expected from chance alone.

The raw score, S, is calculated from the number of gaps and substitutions associated with each aligned sequence wherein higher similarity scores indicate a more significant alignment. Substitution scores are given by a look-up table (see PAM, BLOSUM).

Gap scores are typically calculated as the sum of G, the gap opening penalty and L, the gap extension penalty. For a gap of length n, the gap cost would be G+Ln. The choice of gap costs, G and L is empirical, but it is customary to choose a high value for G (10-15), e.g., 11, and a low value for L (1-2) e.g., 1.

The bit score, S', is derived from the raw alignment score S in which the statistical properties of the scoring system used have been taken into account. Bit scores are normalized with respect to the scoring system, therefore they can be used to compare alignment scores from different searches. The terms "bit score" and "similarity score" are used interchangeably. The bit score gives an indication of how good the alignment is; the higher the score, the better the alignment.

The E-Value, or expected value, describes the likelihood that a sequence with a similar score will occur in the database by chance. It is a prediction of the number of different alignments with scores equivalent to or better than S that are expected to occur in a database search by chance. The smaller the E-Value, the more significant the alignment. For example, an alignment having an E value of $e^{-117}$ that a sequence with a similar score is very unlikely to occur simply by chance. Additionally, the expected score for aligning a random pair of amino acids is required to be negative, otherwise long alignments would tend to have high score independently of whether the segments aligned were related. Additionally, the BLAST algorithm uses an appropriate substitution matrix, nucleotide or amino acid and for gapped alignments uses gap creation and extension penalties. For example, BLAST alignment and comparison of polypeptide sequences are typically done using the BLOSUM62 matrix, a gap existence penalty of 11 and a gap extension penalty of 1.

In one embodiment, sequence similarity scores are reported from BLAST analyses done using the BLOSUM62 matrix, a gap existence penalty of 11 and a gap extension penalty of 1.

In a particular embodiment, sequence identity/similarity scores provided herein refer to the value obtained using GAP Version 10 (GCG, Accelrys, San Diego, Calif.) using the following parameters: % identity and % similarity for a nucleotide sequence using GAP Weight of 50 and Length Weight of 3, and the nwsgapdna.cmp scoring matrix; % identity and % similarity for an amino acid sequence using GAP Weight of 8 and Length Weight of 2, and the BLOSUM62 scoring matrix (Henikoff and Henikoff, *PNAS USA.* 89:10915-10919, 1992). GAP uses the algorithm of Needleman and Wunsch (J Mol Biol. 48:443-453, 1970) to find the alignment of two complete sequences that maximizes the number of matches and minimizes the number of gaps.

In one particular embodiment, the variant polypeptide comprises an amino acid sequence that can be optimally aligned with a reference polypeptide sequence (see, e.g., the Tables, the Sequence Listing; SEQ ID NOs:1, 3, 7-12) to generate a BLAST bit scores or sequence similarity scores of at least about 50, 60, 70, 80, 90, 100, 100, 110, 120, 130, 140, 150, 160, 170, 180, 190, 200, 210, 220, 230, 240, 260, 270, 280, 290, 300, 310, 320, 330, 340, 350, 360, 370, 380, 390, 400, 410, 420, 430, 440, 450, 470, 480, 490, 500, 510, 520, 530, 540, 550, 560, 570, 580, 590, 600, 610, 620, 630, 640, 650, 660, 680, 690, 700, 710, 720, 730, 740, 750, 760, 770, 780, 790, 800, 810, 820, 830, 840, 850, 860, 870, 890, 900, 910, 920, 930, 940, 950, 960, 970, 980, 990, 1000, or more, including all integers and ranges in between, wherein the BLAST alignment used the BLOSUM62 matrix, a gap existence penalty of 11, and a gap extension penalty of 1.

As noted above, a reference polypeptide may be altered in various ways including amino acid substitutions, deletions, truncations, additions, and insertions. Methods for such manipulations are generally known in the art. For example, amino acid sequence variants of a reference polypeptide can be prepared by mutations in the DNA. Methods for mutagenesis and nucleotide sequence alterations are well known in the art. See, for example, Kunkel (*PNAS USA.* 82:488-492, 1985); Kunkel et al., (*Methods in Enzymol.* 154:367-382, 1987), U.S. Pat. No. 4,873,192, Watson, J. D. et al., ("*Molecular Biology of the Gene,*" Fourth Edition, Benjamin/Cummings, Menlo Park, Calif., 1987) and the references cited therein. Guidance as to appropriate amino acid substitutions that do not affect biological activity of the protein of interest may be found in the model of Dayhoff et al., (1978) Atlas of Protein Sequence and Structure (Natl. Biomed. Res. Found., Washington, D.C.).

Methods for screening gene products of combinatorial libraries made by such modifications, and for screening cDNA libraries for gene products having a selected property are known in the art. Such methods are adaptable for rapid screening of the gene libraries generated by combinatorial mutagenesis of reference polypeptides. As one example, recursive ensemble mutagenesis (REM), a technique which enhances the frequency of functional mutants in the libraries, can be used in combination with the screening assays to identify polypeptide variants (Arkin and Yourvan, *PNAS USA* 89:7811-7815, 1992; Delgrave et al., *Protein Engineering.* 6:327-331, 1993).

Also included are antibodies, or antigen-binding fragments thereof, which "competitively inhibit" the binding of the antibodies described herein (see, e.g., Example 1) to a human argininosuccinate synthase polypeptide. Methods for determining mAb specificity and affinity by competitive inhibition can be found, for example, in Harlow, et al., Antibodies: A Laboratory Manual, Cold Spring Harbor Laboratory Press, Cold Spring Harbor, N. Y., 1988), Colligan et al., eds., Current Protocols in Immunology, Greene Publishing Assoc. and Wiley Interscience, N.Y., (1992, 1993); Muller, Meth. Enzymol. 92:589-601, 1983; and Jia, X-C. et al., J. Immunol. Methods 288:91-98, 2004, each of which is incorporated reference.

Particular embodiments include antibodies, or antigen-binding fragments thereof, which competitively inhibit the binding of an antibody to human argininosuccinate synthase (SEQ ID NO:5), where the antibody (which is competitively inhibited) comprises the $V_H$ sequence set forth SEQ ID NO:1, and/or the $V_L$ sequence set forth in SEQ ID NO:3. In specific embodiments, the antibody (which is competitively inhibited) is a monoclonal antibody, for example, a whole monoclonal antibody such as an IgG antibody, as described herein. In particular embodiments, the antibody (which is competitively inhibited) is an IgG1 or IgG2a immunoglobulin subtype.

In certain embodiments, the antibody, or antigen-binding fragment thereof, is conjugated or covalently attached to a detectable entity, for example, to facilitate detection. Exemplary detectable entities include, without limitation, iodine-based labels, radioisotopes, fluorophores/fluorescent dyes, and nanoparticles.

Exemplary iodine-based labels include diatrizoic acid (Hypaque®, GE Healthcare) and its anionic form, diatrizoate. Diatrizoic acid is a radio-contrast agent used in advanced X-ray techniques such as CT scanning. Also included are iodine radioisotopes, described below.

Exemplary radioisotopes that can be used as detectable entities include $^{32}P$, $^{33}P$, $^{35}S$, $^{3}H$, $^{18}F$, $^{11}C$, $^{13}N$, $^{15}O$, $^{111}In$, $^{169}Yb$, $^{99}mTC$, $^{55}Fe$, and isotopes of iodine such as $^{123}I$, $^{124}I$, $^{125}I$, and $^{131}I$. These radioisotopes have different half-lives, types of decay, and levels of energy which can be tailored to match the needs of a particular protocol.

Examples of fluorophores or fluorochromes that can be used as directly detectable entities include fluorescein, tetramethylrhodamine, Texas Red, Oregon Green®, and a number of others (e.g., Haugland, Handbook of Fluorescent Probes—9th Ed., 2002, Molec. Probes, Inc., Eugene Oreg.; Haugland, The Handbook: A Guide to Fluorescent Probes and Labeling Technologies—10th Ed., 2005, Invitrogen, Carlsbad, Calif.). Also included are light-emitting or otherwise detectable dyes. The light emitted by the dyes can be visible light or invisible light, such as ultraviolet or infrared light. In exemplary embodiments, the dye may be a fluorescence resonance energy transfer (FRET) dye; a xanthene dye, such as fluorescein and rhodamine; a dye that has an amino group in the alpha or beta position (such as a naphthylamine dye, 1-dimethylaminonaphthyl-5-sulfonate, 1-anilino-8-naphthalende sulfonate and 2-p-touidinyl-6-naphthalene sulfonate); a dye that has 3-phenyl-7-isocyanatocoumarin; an acridine, such as 9-isothiocyanatoacridine and acridine orange; a pyrene, a bensoxadiazole and a stilbene; a dye that has 3-(s-carboxypentyl)-3'-ethyl-5,5'-dimethyloxacarbocyanine (CYA); 6-carboxy fluorescein (FAM); 5&6-carboxyrhodamine-110 (R110); 6-carboxyrhodamine-6G (R6G); N,N,N',N'-tetramethyl-6-carboxyrhodamine (TAMRA); 6-carboxy-X-rhodamine (ROX); 6-carboxy-4',5'-dichloro-2',7'-dimethoxyfluorescein (JOE); ALEXA FLUOR™; Cy2; Texas Red and Rhodamine Red; 6-carboxy-2',4,7,7'-tetrachlorofluorescein (TET); 6-carboxy-2',4,4',5',7,7'-hexachlorofluorescein (HEX); 5-carboxy-2',4',5',7'-tetrachlorofluorescein (ZOE); NAN; NED; Cy3; Cy3.5; Cy5; Cy5.5; Cy7; and Cy7.5; IR800CW, ICG, Alexa Fluor 350; Alexa Fluor 488; Alexa Fluor 532; Alexa Fluor 546; Alexa Fluor 568; Alexa Fluor 594; Alexa Fluor 647; Alexa Fluor 680, or Alexa Fluor 750.

Nanoparticles usually range from about 1-1000 nm in size and include diverse chemical structures such as gold and silver particles and quantum dots. When irradiated with angled incident white light, silver or gold nanoparticles ranging from about 40-120 nm will scatter monochromatic light with high intensity. The wavelength of the scattered light is dependent on the size of the particle. Four to five different particles in close proximity will each scatter monochromatic light, which when superimposed will give a specific, unique color. Derivatized nanoparticles such as silver or gold particles can be attached to a broad array of molecules including, proteins, antibodies, small molecules, receptor ligands, and nucleic acids. Specific examples of nanoparticles include metallic nanoparticles and metallic nanoshells such as gold particles, silver particles, copper particles, platinum particles, cadmium particles, composite particles, gold hollow spheres, gold-coated silica nanoshells, and silica-coated gold shells. Also included are silica, latex, polystyrene, polycarbonate, polyacrylate, PVDF nanoparticles, and colored particles of any of these materials.

Quantum dots are fluorescing crystals about 1-5 nm in diameter that are excitable by light over a large range of wavelengths. Upon excitation by light having an appropriate wavelength, these crystals emit light, such as monochromatic light, with a wavelength dependent on their chemical composition and size. Quantum dots such as CdSe, ZnSe, InP, or InAs possess unique optical properties; these and similar quantum dots are available from a number of commercial sources (e.g., NN-Labs, Fayetteville, Ark.; Ocean Nanotech, Fayetteville, Ark.; Nanoco Technologies, Manchester, UK; Sigma-Aldrich, St. Louis, Mo.).

Antibodies may be prepared by any of a variety of techniques known to those of ordinary skill in the art. See, e.g., Harlow and Lane, Antibodies: A Laboratory Manual, Cold Spring Harbor Laboratory, 1988. Monoclonal antibodies specific for a polypeptide of interest may be prepared, for example, using the technique of Kohler and Milstein, Eur. J. Immunol. 6:511-519, 1976, and improvements thereto. Also included are methods that utilize transgenic animals such as mice to express human antibodies. See, e.g., Neuberger et al., Nature Biotechnology 14:826, 1996; Lonberg et al., Handbook of Experimental Pharmacology 113:49-101, 1994; and Lonberg et al., Internal Review of Immunology 13:65-93, 1995. Particular examples include the VELOCIMMUNE® platform by REGERNEREX® (see, e.g., U.S. Pat. No. 6,596,541). Antibodies can also be prepared by recombinant techniques, described herein and known in the art.

The antibodies of the present invention can be used in any of the diagnostic and analytical methods and compositions described herein.

Polynucleotides, Host Cells, and Methods of Production

Certain embodiments relate to polynucleotides that encode the antibodies, and antigen-binding fragments thereof, and vectors that comprise such polynucleotides, for example, where the polynucleotides are operably linked to one or more regulatory elements. Also included are recombinant host cells that comprise such polynucleotides, vectors, antibodies, and antigen-binding fragments thereof, in addition to methods of recombinant production of the foregoing.

Antibodies and antigen-binding fragments thereof may be prepared using standard techniques. In particular embodiments, an antibody, or antigen-binding fragment thereof, is expressed as a recombinant protein in an expression system, as described herein and known in the art.

Polynucleotides can contain one or multiple copies of a nucleic acid encoding an antibody, or antigen-binding fragment thereof. In specific embodiments, the polynucleotide sequence comprises at least one sequence in Table 3 below, or a variant or fragment thereof.

TABLE 3

Exemplary Polynucleotide Sequences

| Description | Sequence | SEQ ID NO: |
|---|---|---|
| Heavy chain variable region ($V_H$) | CAGATCCAGTTGGTGCAGTCTGGACCTGA GTTGAAGAAGCCTGGAGAGACAGTCAAGA TCTCCTGCAAGACTTCTGGTTATACCTTC ACAGACTATTCAATACACTGGGTGAAGCA GGCTCCAGGAAAGGGTTTAACGTGGATGG GCTGGATAAACACTGAGACTGGTGAGCCA ACTTATGCAGATGACTTCAAGGGACGCTT TGCCCTCTCTTTGGAAACCTCTGCCAGCA CTGCCTATTTGCAGCTCAAGAACCTCAGA AATGAGGACACGGCTACATATTTCTGTGG TAGTTCTTATTCTTACTGGGGCCAAGGGA CTCTGGTCACTGTCTCTTCA | 2 |
| Light chain variable region ($V_L$) | GATGTTGTGATGACCCAAACTCCACTCTC CCTGCCTGTCAGTCTTGGAGATCAAGCCT CCATCTCTTGCAGGTCTAGTCAGAGCCTT GAAAACAGTAATGGAAAGACCTATTTGAA CTGGTTCCTCCAGAAACCAGGCCAGTCTC CACAGCTCCTGATCTACAGGGTTTCCAAC CGATTTTCTGGGGTCCCAGACAGGTTCAG TGGCAGTGGATCAGGGACTGAATTCACAC TGAAAATCAGCAGAGTGGAGGCTGAGGAT TTGGGAGTTTATTTCTGCCTCCAAGTTAA ACATGTCCCGTGGACGTTCGGTGGAGGCA CCAAGCTGGAAATCAAA | 4 |

Suitable vectors can be chosen or constructed, containing appropriate regulatory sequences, including promoter sequences, terminator sequences, polyadenylation sequences, enhancer sequences, marker genes and other sequences as appropriate. Vectors may be plasmids, viral e.g., phage, or phagemid, as appropriate. For further details see, for example, Molecular Cloning: a Laboratory Manual: 2nd edition, Sambrook et al., 1989, Cold Spring Harbor Laboratory Press. Many known techniques and protocols for manipulation of nucleic acid, for example in preparation of nucleic acid constructs, mutagenesis, sequencing, introduction of DNA into cells and gene expression, and analysis of proteins, are described in detail in Current Protocols in Molecular Biology, Second Edition, Ausubel et al. eds., John Wiley & Sons, 1992, or subsequent updates thereto.

As will be understood by those of skill in the art, it may be advantageous in some instances to produce polypeptide-encoding nucleotide sequences possessing non-naturally occurring codons. For example, codons preferred by a particular prokaryotic or eukaryotic host can be selected to increase the rate of protein expression or to produce a recombinant RNA transcript having desirable properties, such as a half-life which is longer than that of a transcript generated from the naturally occurring sequence. Such polynucleotides are commonly referred to as "codon-optimized." Any of the polynucleotides described herein may be utilized in a codon-optimized form. In certain embodiments, a polynucleotide can be codon optimized for use in specific bacteria such as *E. coli* or yeast such as *S. cerevisiae* (see, e.g., Burgess-Brown et al., *Protein Expr Purif.* 59:94-102, 2008).

In some embodiments, nucleic acids or vectors encoding an antibody, or an antigen-binding fragment thereof, are introduced directly into a host cell, and the cell is incubated under conditions sufficient to induce expression of the encoded polypeptide(s). Therefore, according to certain related embodiments, there is provided a recombinant host cell which comprises a polynucleotide that encodes one or more antibodies, or antigen-binding fragments thereof, described herein, optionally in combination with other components of an antibody (e.g., Fc regions), and which optionally comprise additional exogenous polynucleotides.

Expression of antibodies, or antigen-binding fragments thereof, in the host cell may be achieved by culturing the recombinant host cells (containing the polynucleotide(s)) under appropriate conditions. Following production by expression, the antibodies, or antigen-binding fragments thereof, may be isolated and/or purified using any suitable technique, and then used as desired. The term "host cell" is used to refer to a cell into which has been introduced, or which is capable of having introduced into it, a nucleic acid sequence encoding one or more of the antibodies, or antigen-binding fragments thereof, described herein. The term includes the progeny of the parent cell, whether or not the progeny are identical in morphology or in genetic make-up to the original parent, so long as the selected gene is present. Host cells may be chosen for certain characteristics, for instance, the expression of aminoacyl tRNA synthetase(s) that can incorporate unnatural amino acids into the antibody, or antigen-binding fragment thereof.

Systems for cloning and expression of a heterologous or recombinant protein in a variety of different host cells are well known. Suitable host cells include mammalian cells, bacteria, yeast, and baculovirus systems. Mammalian cell lines available in the art for expression of a proteins include Chinese hamster ovary (CHO) cells, HeLa cells, baby hamster kidney cells, HEK-293 cells, NSO mouse melanoma cells and many others. Additional examples of useful mammalian host cell lines include monkey kidney CV1 line transformed by SV40 (COS-7, ATCC CRL 1651); human embryonic kidney line (293 or 293 cells sub-cloned for growth in suspension culture, Graham et al., *J. Gen Virol.* 36:59 (1977)); baby hamster kidney cells (BHK, ATCC CCL 10); mouse Sertoli cells (TM4, Mather, *Biol. Reprod.* 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TR1 cells (Mather et al., *Annals N.Y. Acad. Sci.* 383:44-68 (1982)); MRC 5 cells; FS4 cells; and a human hepatoma line (Hep G2). Other useful mammalian host cell lines include Chinese hamster ovary (CHO) cells, including DHFR-CHO cells (Urlaub et al., PNAS USA 77:4216 (1980)); and myeloma cell lines such as NSO and Sp2/0. For a review of certain mammalian host cell lines suitable for antibody production, see, e.g., Yazaki and Wu, *Methods in Molecular Biology*, Vol. 248 (B. K. C Lo, ed., Humana Press, Totowa, N. J., 2003), pp. 255-268. Certain preferred mammalian cell expression systems include CHO and HEK293-cell based expression systems including 293F cells. Mammalian expression systems can utilize attached cell lines, for example, in T-flasks, roller bottles, or cell factories, or suspension cultures, for example, in 1 L and 5 L spinners, 5 L, 14 L, 40 L, 100 L and 200 L stir tank bioreactors, or 20/50 L and 100/200 L WAVE bioreactors, among others known in the art.

A common, preferred bacterial host is *E. coli*. The expression of proteins in prokaryotic cells such as *E. coli* is well established in the art. For a review, see for example Pluckthun, A. *Bio/Technology*. 9:545-551 (1991). Expression in eukaryotic cells in culture is also available to those skilled in the art as an option for recombinant production of polypeptides (see Ref, *Curr. Opinion Biotech.* 4:573-576, 1993; and Trill et al., *Curr. Opinion Biotech.* 6:553-560, 1995). In specific embodiments, protein expression may be controlled by a T7 RNA polymerase (e.g., pET vector series). These and related embodiments may utilize the expression host strain BL21(DE3), a λDE3 lysogen of BL21 that supports T7-mediated expression and is deficient in Ion and ompT proteases for improved target protein stability. Also included are expression host strains carrying plasmids encoding tRNAs rarely used in *E. coli*, such as Rosetta™ (DE3) and Rosetta 2 (DE3) strains. Cell lysis and sample handling may also be improved using reagents such as Benzonase® nuclease and BugBuster® Protein Extraction Reagent. For cell culture, auto-inducing media can improve the efficiency of many expression systems, including high-throughput expression systems. Media of this type (e.g., Overnight Express™ Autoinduction System) gradually elicit protein expression through metabolic shift without the addition of artificial inducing agents such as IPTG. Particular embodiments employ hexahistidine tags (such as His•Tag® fusions), followed by immobilized metal affinity chromatography (IMAC) purification, or related techniques. In certain aspects, however, clinical grade proteins can be isolated from *E. coli* inclusion bodies, without or without the use of affinity tags (see, e.g., Shimp et al., *Protein Expr Purif.* 50:58-67, 2006). As a further example, certain embodiments may employ a cold-shock induced *E. coli* high-yield production system, because over-expression of proteins in *Escherichia coli* at low temperature improves their solubility and stability (see, e.g., Qing et al., *Nature Biotechnology*. 22:877-882, 2004).

In addition, a host cell strain may be chosen for its ability to modulate the expression of the inserted sequences or to process the expressed protein in the desired fashion. Such modifications of the polypeptide include, but are not limited to, post-translational modifications such as acetylation, carboxylation, glycosylation, phosphorylation, lipidation, and acylation. Post-translational processing, which cleaves a "prepro" form of the protein may also be used to facilitate correct insertion, folding and/or function. Different host cells such as yeast, CHO, HeLa, MDCK, HEK293, and W138, in addition to bacterial cells, which have or even lack specific cellular machinery and characteristic mechanisms for such post-translational activities, may be chosen to ensure the correct modification and processing of the protein (e.g., antibody) of interest.

For long-term, high-yield production of recombinant proteins, stable expression is generally preferred. For example, cell lines that stably express a polynucleotide of interest may be transformed using expression vectors which may contain viral origins of replication and/or endogenous expression elements and a selectable marker gene on the same or on a separate vector. Following the introduction of the vector, cells may be allowed to grow for about 1-2 days in an enriched media before they are switched to selective media. The purpose of the selectable marker is to confer resistance to selection, and its presence allows growth and recovery of cells which, successfully express the introduced sequences. Resistant clones of stably transformed cells may be proliferated using tissue culture techniques appropriate to the cell type. Transient production, such as by transient transfection or infection, can also be employed. Exemplary mammalian expression systems that are suitable for transient production include HEK293 (e.g., 293F cells) and CHO-based systems.

Host cells transformed with a polynucleotide sequence of interest may be cultured under conditions suitable for the expression and recovery of the protein from cell culture. Certain specific embodiments utilize serum free cell expression systems. Examples include HEK293 cells and CHO cells that can grow on serum free medium (see, e.g., Rosser et al., *Protein Expr. Purif.* 40:237-43, 2005; and U.S. Pat. No. 6,210,922).

The protein(s) produced by a recombinant cell can be purified and characterized according to a variety of techniques known in the art. Exemplary systems for performing protein purification and analyzing protein purity include fast protein liquid chromatography (FPLC) (e.g., AKTA and Bio-Rad FPLC systems), high-performance liquid chromatography (HPLC) (e.g., Beckman and Waters HPLC). Exemplary chemistries for purification include ion exchange chromatography (e.g., Q, S), size exclusion chromatography, salt gradients, affinity purification (e.g., Ni, Co, FLAG, maltose, glutathione, protein A/G), gel filtration, reverse-phase, ceramic HyperD® ion exchange chromatography, and hydrophobic interaction columns (HIC), among others known in the art. Also included are analytical methods such as SDS-PAGE (e.g., coomassie, silver stain), immunoblot, Bradford, and ELISA, which may be utilized during any step of the production or purification process, typically to measure the purity of the protein composition.

Also included are methods of concentrating recombinantly produced proteins, e.g., antibodies. Examples include lyophilization, which is typically employed when the solution contains few soluble components other than the protein of interest. Lyophilization is often performed after HPLC run, and can remove most or all volatile components from the mixture. Also included are ultrafiltration techniques, which typically employ one or more selective permeable membranes to concentrate a protein solution. The membrane allows water and small molecules to pass through and retains the protein; the solution can be forced against the membrane by mechanical pump, gas pressure, or centrifugation, among other techniques.

In certain embodiments, the antibodies, or antigen-binding fragments thereof, have a purity of at least about 90%, as measured according to routine techniques in the art. In certain embodiments, such as diagnostic compositions or certain therapeutic compositions, the antibodies, or antigen-binding fragments thereof, have a purity of at least about 95%. In specific embodiments, such as therapeutic or pharmaceutical compositions, the antibodies, or antigen-binding fragments thereof, have a purity of at least about 97% or 98% or 99%. In other embodiments, such as when being used as reference or research reagents, the antibodies, or antigen-binding fragments thereof, can be of lesser purity, and may have a purity of at least about 50%, 60%, 70%, or 80%. Purity can be measured overall or in relation to selected components, such as other proteins, e.g., purity on a protein basis.

In certain embodiments, the compositions described here are about substantially endotoxin free, including, for example, about 95% endotoxin free, preferably about 99% endotoxin free, and more preferably about 99.99% endotoxin free. The presence of endotoxins can be detected according to routine techniques in the art, as described herein. In specific embodiments, the antibodies, or antigen-binding fragments thereof, are made from a eukaryotic cell such as a mammalian or human cell in substantially serum free media.

Methods of Use

Embodiments of the present invention include methods of using the antibodies described herein, and antigen-binding fragments thereof, to determine the presence, absence, amount or levels of an argininosuccinate synthase polypeptide in a sample, such as a biological sample. Such methods include, for example, the use of the antibodies, or antigen-binding fragments thereof, as a companion diagnostic to identify a subject for arginine deprivation therapy, including for the administration of at least one arginine depletion agent. In some embodiments, the subject is considered suitable for arginine deprivation therapy if the amount of argininosuccinate synthase polypeptide in a biological sample is reduced relative to a control. In particular embodiments, the methods include using the antibodies, or antigen-binding fragment thereof, as a companion diagnostic to identify a subject having or suspected of having a cancer or tumor that exhibits a deficiency of argininosuccinate synthase (e.g., reduced expression of argininosuccinate synthase), and treating or causing the subject to be treated with arginine deprivation therapy.

Certain embodiments therefore include methods of determining an amount of human argininosuccinate synthase polypeptide in a biological sample, comprising (a) obtaining or receiving a biological sample, optionally from a subject, (b) contacting the biological sample with an antibody described herein, or an antigen-binding fragment thereof, and (c) measuring the amount of the antibody, or antigen-binding fragment thereof, in the sample, where the amount of the antibody, or antigen-binding fragment thereof, determines the amount of the argininosuccinate synthase polypeptide in the sample.

Also included are methods of identifying a deficiency of argininosuccinate synthase in a biological sample, comprising (a) obtaining or receiving a biological sample, optionally from a subject, (b) contacting the biological sample with an antibody described herein, or antigen-binding fragment thereof, (c) measuring the amount of the antibody, or antigen-binding fragment thereof, in the sample, where the amount of the antibody, or antigen-binding fragment thereof, determines the amount of argininosuccinate synthase polypeptide in the sample, and (d) identifying a deficiency of argininosuccinate synthase in the sample if the amount of the argininosuccinate synthase polypeptide in the biological sample is reduced relative to a control.

Some embodiments include methods of identifying a subject for arginine deprivation or depletion therapy, comprising (a) obtaining or receiving a biological sample from the subject, optionally via a healthcare provider, (b) contacting the biological sample with an antibody described herein, or antigen-binding fragment thereof, (c) measuring the amount of the antibody, or antigen-binding fragment thereof, in the sample, where the amount of the antibody, or antigen-binding fragment thereof, determine s the amount of argininosuccinate synthase polypeptide in the sample, and (d) identifying the subject as suitable for arginine deprivation therapy if the amount of the argininosuccinate synthase polypeptide in the biological sample is reduced relative to a control.

In some embodiments, step (a) comprises receiving the biological sample from a healthcare provider, such as a physician, clinic, or hospital. The entity receiving the biological sample and/or performing the testing can be associated with or separate from the healthcare provider. In particular embodiments, the entity receiving the sample and/or performing the testing is a third party diagnostic company. In some embodiments, the entity receiving the sample and/or performing the testing is a clinical or hospital-associated diagnostic laboratory. In some embodiments, the method (e.g., step (c) or (d)) comprises providing information to the same or different healthcare provider (e.g., physician) on the amount of the argininosuccinate synthase polypeptide in the biological sample.

Any of these and related embodiments can further comprise administering to the subject of (d) at least one arginine depletion agent, as described herein and/or known in the art.

Also included are methods for diagnosing and treating a subject comprising, (a) analyzing the results of a test that indicates the amount of argininosuccinate synthase polypeptide in a biological sample from the subject, where the test is performed using an antibody described herein, or antigen-binding fragment thereof, (b) diagnosing the patient as suitable for arginine deprivation therapy if the results from (a) indicate that the amount of argininosuccinate synthase polypeptide in the biological sample is reduced relative to a control, and (c) treating the subject of (b) by administering at least one arginine depletion agent.

A method for treating a subject, comprising (a) requesting a test that determines the amount of argininosuccinate synthase polypeptide in a biological sample from the subject, where the test is performed using an antibody described herein, or an antigen-binding fragment thereof, and (b) administering to the subject at least one arginine depletion agent if the test from (a) indicates that the amount of argininosuccinate synthase polypeptide in the biological sample is reduced relative to a control.

In particular embodiments, the subject is a mammal, for example, a human patient.

In certain embodiments, the subject has or is suspected of having a cancer or tumor. Examples of cancers and tumors include melanomas, hepatomas, pancreatic cancers, prostate cancers, mesotheliomas, sarcomas, head and neck cancers, leukemias, acute myeloid leukemias, relapsed acute myeloid leukemias, breast cancers, ovarian cancers, colorectal cancers, gastric cancers, gliomas, glioblastoma multiforme, non-small cell lung cancers (NSCLC), kidney cancers such as renal cell carcinomas, bladder cancers, uterine cancers, esophageal cancers, brain cancers, cervical cancers, testicular cancers, and stomach cancers.

The term "melanoma" includes a malignant or benign tumor arising from the melanocytic system of the skin and other organs, including the oral cavity, esophagus, anal canal, vagina, leptomeninges, and/or the conjunctiva or eye. The term "melanoma" includes, as non-limiting examples, acral-lentiginous melanoma, amelanotic melanoma, benign juvenile melanoma, lentigo maligna melanoma, malign melanoma, nodular melanoma, subungual melanoma, and superficial spreading melanoma.

A "hepatoma" may be a malignant or benign tumor of the liver, including as non-limiting examples, hepatocellular carcinoma, malignant liver tumor, fibrolamellar hepatoma, and hepatocellular cholangiocarcinoma, mixed hepatocellular cholangiocarcinoma, and undifferentiated hepatocellular carcinoma.

The term "sarcoma" includes a malignant or benign tumor arising in the connective tissue including as non-limiting examples, bones, cartilage, and striated muscle. Examples of sarcomas include, but are not limited to, liposarcomas, leiomyosarcomas, rhabdomyosarcoma, synovial sarcoma, angiosarcomas, fibrosarcomas, neurofibrosarcomas, gastrointestinal stromal tumors (GIST), Ewing's Sarcomas, osteosarcomas, and chondrosarcomas.

"Breast cancer" refers to a malignant or benign tumor arising in the breast, and includes, but is not limited to, local stage breast cancers, regional stage tumors, and distant stage cancers. Examples of breast cancers include, but are not limited to, adenocarcinomas (including ductal carcinomas and lobular carcinomas), lobular carcinoma in situ (LCIS) medullary carcinomas, mucinous carcinomas, Paget's disease of the nipple, Phyllodes tumors, and tubular carcinomas.

More particular examples of such cancers include squamous cell cancer, small-cell lung cancer, pituitary cancer, esophageal cancer, astrocytoma, soft tissue sarcoma, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma, brain cancer, endometrial cancer, testis cancer, cholangiocarcinoma, gallbladder carcinoma, gastric cancer, melanoma, and various types of head and neck cancer. In particular embodiments, the cancer is cancer of the breast, brain, prostate, kidney, pancreas, lung, thyroid, colon, cervix, ovary, testes, rectum, gall bladder, anus, spleen, liver, skin, bone, pituitary, endometrium, stomach, blood, or lymph gland.

The biological sample can include any variety of samples, fluids, or tissues. Non-limiting examples of biological samples include blood, plasma, skin, hair, hair follicles, saliva, oral mucous, vaginal mucous, sweat, tears, epithelial tissues, urine, semen, seminal fluid, seminal plasma, prostatic fluid, excreta, biopsy, ascites, cerebrospinal fluid, lymph, tissue extracts sample, and biopsy samples, such as cancer or tumor biopsy sample, or a suspected cancer or tumor biopsy sample. Specific examples if cancerous or tumor biopsy samples include those from skin tissue, liver tissue, pancreatic tissue, prostate tissue, mesothelial tissue, epithelial tissue, ovarian tissue, colorectal tissue, gastric tissue, brain tissue, lung tissue, kidney tissue, bladder tissue, uterine tissue, esophageal tissue, cervical tissue, testicular tissue, breast tissue, and mesenchymal tissue such as bone tissue, cartilage tissue, fat tissue, muscle tissue, vascular tissue, blood, and hematopoietic cells/tissue.

In some embodiments, the biological sample is identified as having a deficiency of a argininosuccinate synthase, or a subject is identified or diagnosed as suitable for arginine deprivation therapy, if the amount or level of the argininosuccinate synthase polypeptide in the biological sample is reduced relative to a control. In some embodiments, the control is a reference standard, a biological sample from a healthy subject, or a healthy biological sample from the same subject. In some embodiments, the control is a non-cancerous biological sample from the same subject, for instance, from the same tissue type as the cancer or suspected cancer.

In particular embodiments, for instance, to identify a subject for arginine deprivation therapy, the amount or level of argininosuccinate synthase polypeptide in the biological sample is reduced relative to a control (e.g., non-cancerous tissue, reference standard) by a statistically significant amount. Merely by way of illustration, in some aspects the amount or level of argininosuccinate synthase polypeptide in the biological sample is reduced relative to the control by about or at least about 10%, 20%, 30%, 40%, 50%, 60%, 70%, 80%, 90%, or 100%, including all integers and ranges in between. In specific embodiments, the amount or level of argininosuccinate synthase polypeptide in the biological sample is undetectable or substantially undetectable.

The presence, absence, amount, or levels of an antibody and thus an argininosuccinate synthase polypeptide in a sample can be measured according to any variety of techniques in the art. For instance, certain embodiments may employ standard methodologies and detectors. Examples include immunohistochemistry (IHC), western blotting, immunoprecipitation, enzyme-linked immunosorbent assays (ELISA), slot blotting, and peptide mass fingerprinting. Certain embodiments may employ cell-sorting or cell visualization or imaging devices/techniques to detect or quantitate the amount or levels of an antibody. Examples include flow cytometry (or FACS), immunofluorescence analysis (IFA), and in situ hybridization techniques, such as fluorescent in situ hybridization (FISH).

Certain embodiments may employ conventional biology methods, software, and systems for diagnostic purposes. Computer software products or method typically include or use computer readable medium having computer-executable instructions for performing the logic steps of the method. Suitable computer readable medium include floppy disk, CD-ROM/DVD/DVD-ROM, hard-disk drive, flash memory, ROM/RAM, magnetic tapes, etc. The computer executable instructions may be written in a suitable computer language or combination of several languages. Basic computational biology methods are described in, for example Setubal and Meidanis et al., Introduction to Computational Biology Methods (PWS Publishing Company, Boston, 1997); Salzberg, Searles, Kasif, (Ed.), Computational Methods in Molecular Biology, (Elsevier, Amsterdam, 1998); Rashidi and Buehler, Bioinformatics Basics: Application in Biological Science and Medicine (CRC Press, London, 2000) and Ouelette and Bzevanis Bioinformatics: A Practical Guide for Analysis of Gene and Proteins (Wiley & Sons, Inc., 2nd ed., 2001). See also U.S. Pat. No. 6,420,108.

Also included are methods of treating a subject with an arginine deprivation or depletion therapy. In some embodiments, the arginine deprivation or depletion therapy includes the administration of an arginine depletion agent. Non-limiting examples of arginine depletion agents include arginine deiminase (ADI) polypeptides, arginase polypeptides, arginine decarboxylase polypeptides, and arginine kinase polypeptides.

In particular embodiments, the arginine depletion agent is an ADI polypeptide, for example, a recombinant ADI polypeptide. Examples of therapeutic ADI polypeptides are described, for example, in WO 2013/151568; and U.S. application Ser. Nos. 14/214,040; 13/214,398; 10/645,723; 10/757,843; which are incorporated by reference in their entireties. The ADI polypeptide may be derived, cloned, or produced from any source, including, for example, microorganisms, recombinant biotechnology or any combination thereof. For example, ADI genes and polypeptides may be cloned and prepared from microorganisms of the genera *Mycoplasma, Clostridium, Bacillus, Borrelia, Enterococcus, Streptococcus, Lactobacillus*, and *Giardia*. In certain embodiments, the ADI polypeptide is from *Mycoplasma pneumoniae, Mycoplasma hominis, Mycoplasma arginini, Steptococcus pyogenes, Steptococcus pneumoniae, Borrelia burgdorferi, Borrelia afzelii, Giardia intestinalis, Clostridium perfringens, Bacillus licheniformis, Enterococcus faecalis, Lactobacillus sake*, or any combination thereof.

In certain embodiments, the ADI polypeptide is from a microorganism of the genus Mycoplasma. In some embodiments, the ADI is from *Mycoplasma hominis, Mycoplasma arthritides, Mycoplasma arginine*, or any combination thereof. In particular embodiments, the ADI polypeptide comprises the amino acid sequence of SEQ ID NO: 6 (ADI from *Mycoplasma hominis*, see Table 4 below), or a variant or fragment thereof having ADI activity (e.g., able to metabolize arginine into citrulline and ammonia). In certain embodiments, the ADI polypeptide is modified (e.g., by substitution, deletion) to remove at least one lysine at position 112, 374, 405, and/or 408 of SEQ ID NO:6.

TABLE 4

Exemplary ADI Sequence(s)

| Description | Sequence | SEQ ID NO: |
|---|---|---|
| ADI from M. Hominis | MSVFDSKFNGIHVYSEIGELETVLVHEPGR EIDYITPARLDELLFSAILESHDARKEHQS FVKIMKDRGINVVELTDLVAETYDLASKAA KEEFIETFLEETVPVLTEANKKAVRAFLLS KPTHEMVEFMMSGITKYELGVESENELIVD PMPNLYFTRDPFASVGNGVTIHFMRYIVRR RETLFARFVFRNHPKLVKTPWYYDPAMKMP IEGGDVFIYNNETLVVGVSERTDLDTITLL AKNIKANKEVEFKRIVAINVPKWTNLMHLD TWLTMLDKNKFLYSPIANDVFKFWDYDLVN GGAEPQPQLNGLPLDKLLASIINKEPVLIP IGGAGATEMEIARETNFDGTNYLAIKPGLV IGYDRNEKTNAALKAAGITVLPFHGNQLSL GMGNARCMSMPLSRKDVKW | 6 |

Native ADI may be found in microorganisms and is antigenic and rapidly cleared from circulation in a patient. These problems may be overcome by modifying ADI. Thus, in certain embodiments, the ADI polypeptide comprises (e.g., is covalently attached to) a modifying agent, including, but not limited to macromolecule polymers, proteins, peptides, polysaccharides, or other compounds. The ADI polypeptide and the modifying agent may be linked by either covalent bonds or non-covalent interaction to form a stable conjugate or a stable composition to achieve a desired effect. In certain embodiments, the modified ADI polypeptide retains the biological activity of ADI and has a longer half-life in vivo and lower antigenicity relative to the unmodified ADI. In some embodiments, the ADI polypeptide is covalently bonded via a linking group to polyethylene glycol. In specific embodiments, the ADI polypeptide is ADI-PEG 20.

In some embodiments, the arginine depletion agent is an arginase I polypeptide, for example, a recombinant arginase I polypeptide. In specific embodiments, the arginase I polypeptide comprises at least 50 contiguous amino acids of a human arginase I protein (see UniProt: P05089). In particular embodiments, the arginine depletion agent is an arginase II polypeptide, for example, a recombinant arginase II polypeptide. In particular embodiments, the recombinant human arginase II polypeptide comprises at least 50 contiguous amino acids of a human arginase II protein (see UniProt: P78540). In some embodiments, the arginine depletion agent is an arginase polypeptide that comprises a metal cofactor such as a cobalt atom or a manganese atom. In certain embodiments, the cobalt-containing arginase polypeptide is a polypeptide as described, for example, in WO 2010/051533.

In some embodiments, the arginine depletion agent is an arginine decarboxylase polypeptide, for example, a recombinant arginine decarboxylase polypeptide. In some embodiments, the arginine depletion agent comprises at least 50 contiguous amino acids of human arginine decarboxylase (see UniProt: Q96A70).

In particular embodiments, the arginine depletion agent is a pegylated polypeptide.

In some instances, the methods provided herein may include administering to the subject one or more chemotherapeutic or other anti-cancer agents prior to, concurrently with, or following administration of the arginine depletion agent. In certain embodiments, the subject to be treated with arginine deprivation therapy is undergoing, has undergone, or is about to undergo surgery, radiation therapy, immunotherapy, and/or hormone therapy.

Compositions and Kits

Also included are compositions that comprise the antibodies, or antigen-binding fragments thereof, described herein, optionally in combination with a suitable carrier. A composition or carrier may be liquid, semi-liquid, semi-solid, or solid.

Solutions or suspensions may include, for example, a sterile diluent (such as water), saline solution (e.g., phosphate buffered saline (PBS), physiological saline, Ringer's solution, isotonic sodium chloride), fixed oil, polyethylene glycol, glycerin, propylene glycol or other synthetic solvent; antimicrobial agents (such as benzyl alcohol and methyl parabens); antioxidants (such as ascorbic acid and sodium bisulfite), chelating agents (such as ethylenediaminetetraacetic acid (EDTA)); and/or buffers (such as acetates, citrates, phosphates, and other organic acids), including combinations of the foregoing. Also included as suitable carriers are solutions containing thickening and solubilizing agents, such as glucose, polyethylene glycol, polypropylene glycol and mixtures thereof. A surfactant may be added to facilitate the formation of a homogeneous solution or suspension. Surfactants are compounds that non-covalently interact with the antibody, or antigen-binding fragment thereof, so as to facilitate dissolution or homogeneous suspension of the conjugate in the aqueous system.

Additional examples of carriers include low molecular weight (e.g., less than about 10 residues) polypeptides or peptides; proteins such as serum albumin, gelatin, or immunoglobulins; hydrophilic polymers such as polyvinylpyrrolidone; amino acids such as glycine, glutamine, asparagine, arginine, or lysine; monosaccharides, disaccharides, and other carbohydrates including glucose, mannose, or dextrins; sugar alcohols such as mannitol or sorbitol; salt-forming counterions such as sodium; and/or nonionic surfactants such as polysorbate 20 (TWEEN™) polyethylene glycol (PEG), and poloxamers (PLURONICS™), and the like.

In some embodiments, the antibody, or antigen-binding fragment thereof, is entrapped in microcapsules prepared, for example, by coacervation techniques or by interfacial polymerization (for example, hydroxymethylcellulose or gelatin-microcapsules and poly-(methylmethacylate)microcapsules, respectively), in colloidal drug delivery systems (for example, liposomes, albumin microspheres, microemulsions, nano-particles and nanocapsules), or in macroemulsions. Such techniques are disclosed in Remington's Pharmaceutical Sciences, 16th edition, Oslo, A., Ed., (1980). The particle(s) or liposomes may further comprise other diagnostic agents, such as detectable entities.

In particular embodiments, the antibody, or antigen-binding fragment thereof, is a freeze-dried or lyophilized, cryo-desiccated. These terms refer to a dehydration process of freezing the antibody composition and then reducing the surrounding pressure to allow the frozen water in the composition to sublimate directly from the solid phase to the gas phase. Also included are solid compositions such as powders, granules, compressed tablets, pills, capsules, and the like. In some embodiments, solid composition contain one or more inert diluents or edible carriers. In certain embodiments, one or more of the following may be present: binders such as carboxymethylcellulose, ethyl cellulose, microcrystalline cellulose, gum tragacanth or gelatin; and excipients such as starch, lactose or dextrins, disintegrating agents such as alginic acid, sodium alginate, Primogel, corn starch and the like.

Certain embodiments include kits, comprising one or more of the antibodies, or antigen-binding fragments thereof, as described herein, optionally in one or more containers. The kits can include written instructions on how to use and/or prepare the antibodies for use, for example, as detection and/or diagnostic agents. In some embodiments, the written instructions describe how to use the antibodies, or antigen-binding fragments thereof, to identify a subject for arginine deprivation therapy, e.g., with arginine depletion agent(s). In some embodiments, the kit comprises material(s) for an enzyme-linked immunosorbent assay (ELISA) or similar assay, for example, where the antibody, or antigen-binding fragment thereof, is attached or attachable to a solid substrate for performing an ELISA or similar assay. In some embodiments, the kit comprises material(s) for an immunohistochemistry (IHC) assay.

The kits herein may also include a one or more additional therapeutic agents or other components suitable or desired for the indication being treated, or for the desired diagnostic application. An additional therapeutic agent may be contained in a second container, if desired. Examples of additional therapeutic agents arginine depletion agents such as arginine deiminase (ADI) polypeptides, arginase polypeptides, arginine decarboxylase polypeptides, and arginine kinase polypeptides, for example, as described herein. In specific embodiments, the arginine depletion agent is ADI-PEG 20.

The following Examples are offered by way of illustration and not by way of limitation.

EXAMPLES

Example 1

Sequencing and Characterization of Hybridoma Antibody Directed Against Argininosuccinate Synthase Experiments were performed to identify the $V_H$ and $V_L$ sequences of a hybridoma antibody clone directed against the protein argininosuccinate synthase. Enzyme linked immunosorbent assay (ELISA) analysis was performed to determine the hybridoma subtype as mouse IgG2A (see FIG. 1). RNA was then extracted from the hybridoma cells, and the variable regions of the heavy and light chains were amplified by polymerase chain reaction (PCR) and subcloned into a mouse IgG1 expression vector.

To characterize the $V_H$ sequence, the amino acid sequences of six productive sub-clones were identified and aligned (see FIG. 2A). To characterize the $V_L$ sequences, the amino acid sequences of five productive sub-clones were identified and aligned (see FIG. 2B). Based on the sequence similarity among these clones, the $V_H$ and $V_L$ nucleotide and amino acid sequences were determined, as shown in Table E1 below.

TABLE E1

V_H and V_L Sequences

| Description | Sequence | SEQ ID NO: |
|---|---|---|
| Amino acid sequence of V_H Chain | QIQLVQSGPELKKPGETVKISCKTSGYTF TDYSIHWVKQAPGKGLTWMGWINTETGEP TYADDFKGRFALSLETSASTAYLQLKNLR NEDTATYFCGSSYSYWGQGTLVTVSS | 1 |
| Polynucleotide sequence of V_H Chain | CAGATCCAGTTGGTGCAGTCTGGACCTGA GTTGAAGAAGCCTGGAGAGACAGTCAAGA TCTCCTGCAAGACTTCTGGTTATACCTTC ACAGACTATTCAATACACTGGGTGAAGCA GGCTCCAGGAAAGGGTTTAACGTGGATGG GCTGGATAAACACTGAGACTGGTGAGCCA ACTTATGCAGATGACTTCAAGGGACGCTT TGCCCTCTCTTTGGAAACCTCTGCCAGCA CTGCCTATTTGCAGCTCAAGAACCTCAGA AATGAGGACACGGCTACATATTTCTGTGG TAGTTCTTATTCTTACTGGGGCCAAGGGA CTCTGGTCACTGTCTCTTCA | 2 |
| Amino acid sequence of V_L Chain | DVVMTQTPLSLPVSLGDQASISCRSSQSL ENSNGKTYLNWFLQKPGQSPQLLIYRVSN RFSGVPDRFSGSGSGTEFTLKISRVEAED LGVYFCLQVKHVPWTFGGGTKLEIK | 3 |
| Polynucleotide sequence of V_L Chain | GATGTTGTGATGACCCAAACTCCACTCTC CCTGCCTGTCAGTCTTGGAGATCAAGCCT CCATCTCTTGCAGGTCTAGTCAGAGCCTT GAAAACAGTAATGGAAAGACCTATTTGAA CTGGTTCCTCCAGAAACCAGGCCAGTCTC CACAGCTCCTGATCTACAGGGTTTCCAAC CGATTTTCTGGGGTCCCAGACAGGTTCAG TGGCAGTGGATCAGGGACTGAATTCACAC TGAAAATCAGCAGAGTGGAGGCTGAGGAT TTGGGAGTTTATTTCTGCCTCCAAGTTAA ACATGTCCCGTGGACGTTCGGTGGAGGCA CCAAGCTGGAAATCAAA | 4 |

Figure 3:
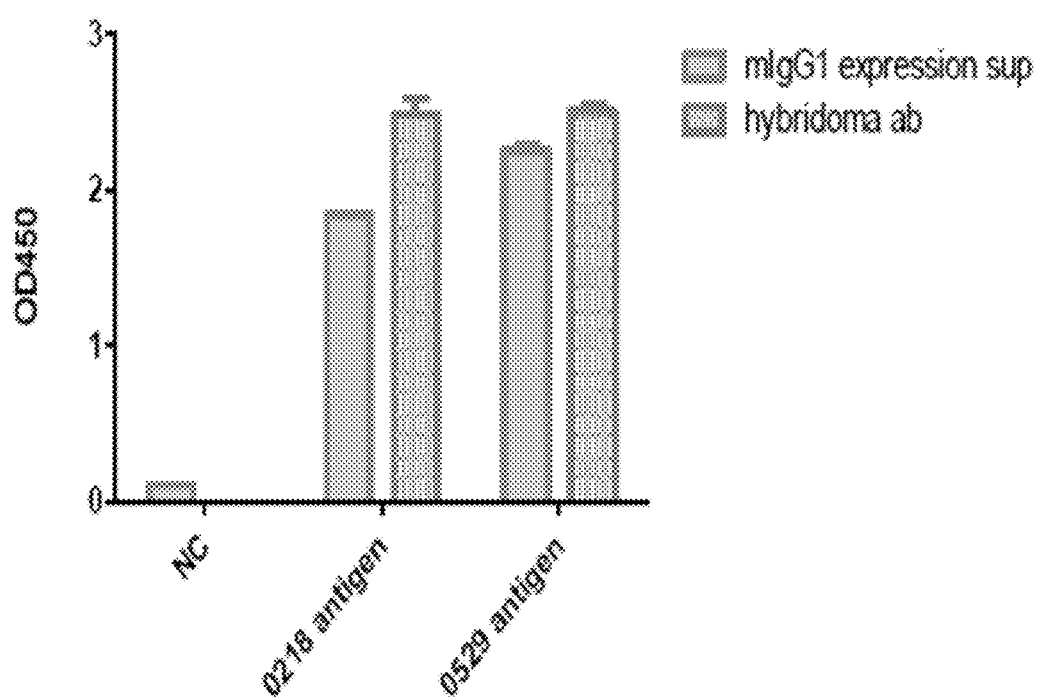
FIG. 3 shows that the sub-cloned $V_H$ and $V_L$ sequences bind to argininosuccinate synthase antigens at levels comparable to the original hybridoma.

The subcloned V_H and V_L sequences (in the mouse IgG1 expression vector) were recombinantly expressed in 293F cells, isolated, and tested by ELISA for binding to argininosuccinate synthase antigens, relative to the original hybridoma. As shown in FIG. 3, the V_H and V_L sequences from Table E1 above showed strong specific binding to argininosuccinate synthase antigens 0218 and 0529.

Example 2

Detection of Argininosuccinate Synthase in Clinical Samples by Immunohistochemistry Experiments were performed to determine the accuracy and precision of immunohistochemistry assays for detecting expression levels of argininosuccinate synthase in a variety of clinical samples. Monoclonal antibodies against argininosuccinate synthase (see Example 1) were used in combination with the Leica Bond Polymer Refine Detection Kit to detect expression in over 100 different tissues, including normal tissues and a variety of tumor tissues such as liver tumor (e.g., hepatocellular carcinoma), lymphoma, renal cell carcinoma, rhabdomyosarcoma, neuroblastoma, seminoma, melanoma, bone marrow (AML), colon carcinoma, lung carcinoma, thyroid carcinoma, uterine carcinoma, gastric carcinoma, brain carcinoma, and breast carcinoma. The clinical sample cohort consisted of 103 total tissues: 60 positive tissues and 43 negative tissues.

Argininosuccinate synthase immunoreactivity is typically located in the cytoplasm, but nuclear staining may also be observed. Interpretation of the stains were performed manually by a pathologist. The percentage of tumor cells with positive staining and the average stain intensity were reported.

Methods.

Formalin-fixed, paraffin-embedded specimens were sectioned at 4-5 µm and mounted on positively charged slides. Slides were air dried and then placed in a 60° C. oven for 60 minutes. Slides were stained using the Leica Bond III instrument. Paraffin was removed from the slides using the standard Leica Bond dewax protocol. The tissue was antigen retrieved with either Bond ER1 for 5 or Bond ER2 for 20 minutes.

Mouse anti-argininosuccinate synthase monoclonal antibody was applied to the slide at a concentration of 0.625 µg/mL and incubated for 15 min or 0.4 µg/mL and incubated for 30 minutes. The Leica Bond Polymer Refine Detection kit was used to visualize the staining—post primary for 8 minutes and polymer for 8 minutes. The slides were then treated with Peroxide Block for five minutes followed by Mixed DAB Refine for ten minutes. Stained sections were counterstained with hematoxylin for 7 The slides were then dehydrated and cover-slipped.

Results.

Overall, 60 out of the 103 samples showed consistent positive cytoplasmic staining of the epithelial and endothelial cells, whereas the tumor cells in various tumor types did not show expression of argininosuccinate synthase. The staining patterns in tumor vs. normal tissues agreed with that reported in the literature in all instances. Inter-assay reproducibility studies showed 100% concordance between staining batches. Positive and negative samples as reported in the literature were tested multiple times and were consistent with the literature. There was no significant staining differences observed between decalcified and non-decalcified samples.

Figure 4:
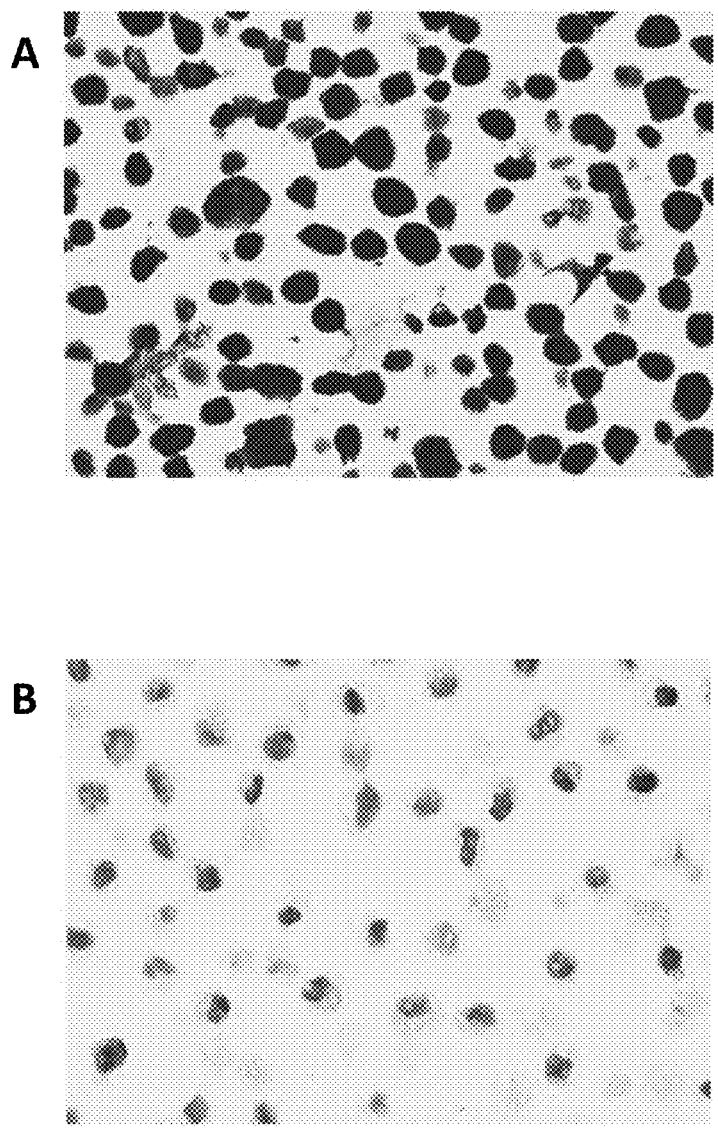
FIG. 4 shows the detection of argininosuccinate synthase expression in human cancer cell lines A431 (FIG. 4A) and SKMEL-3 (FIG. 4B) by immunohistochemical staining (immunohistochemistry; IHC) with anti-argininosuccinate synthase monoclonal antibody.
Figure 5:
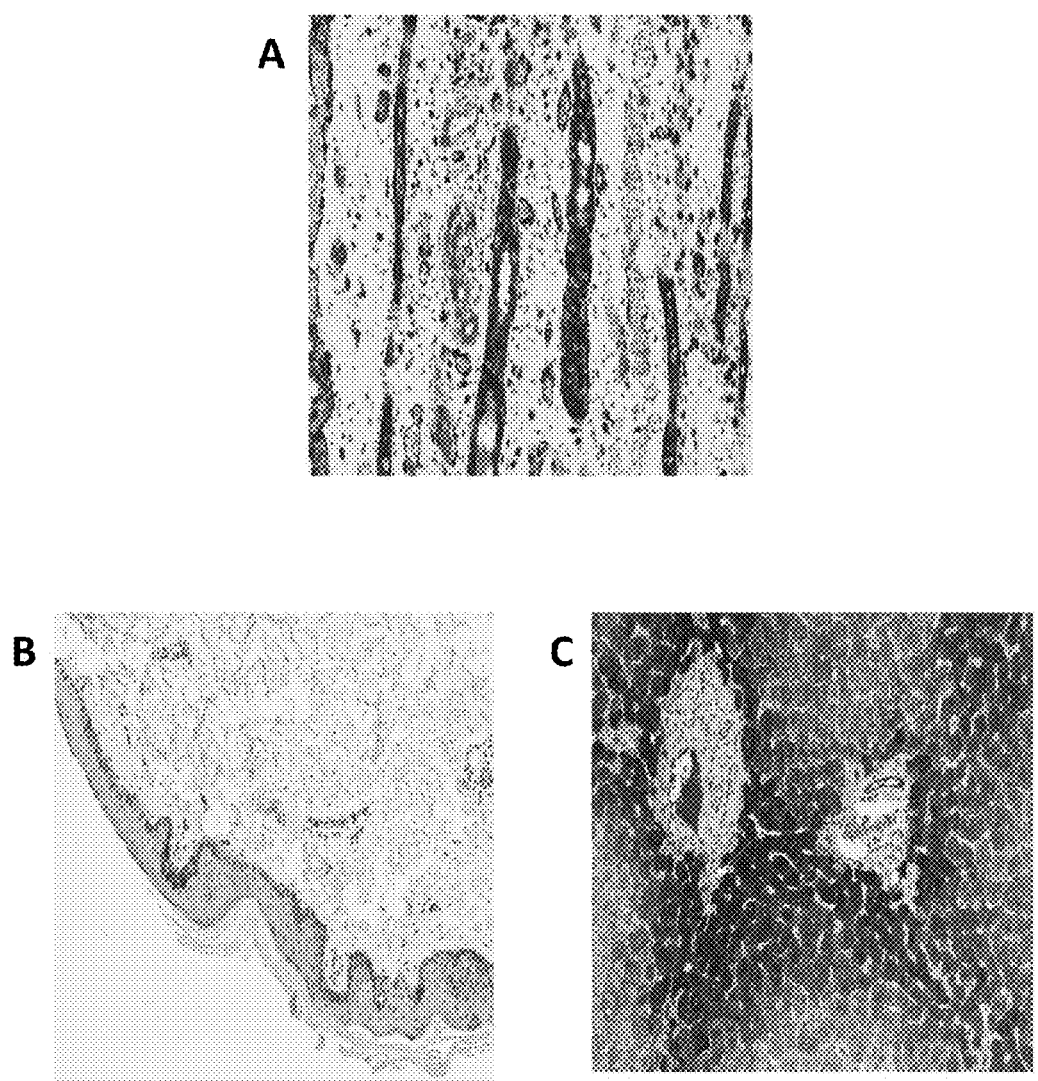
FIG. 5 shows the detection of argininosuccinate synthase expression in normal human tissues (FIG. 5A, kidney.
Figure 6:
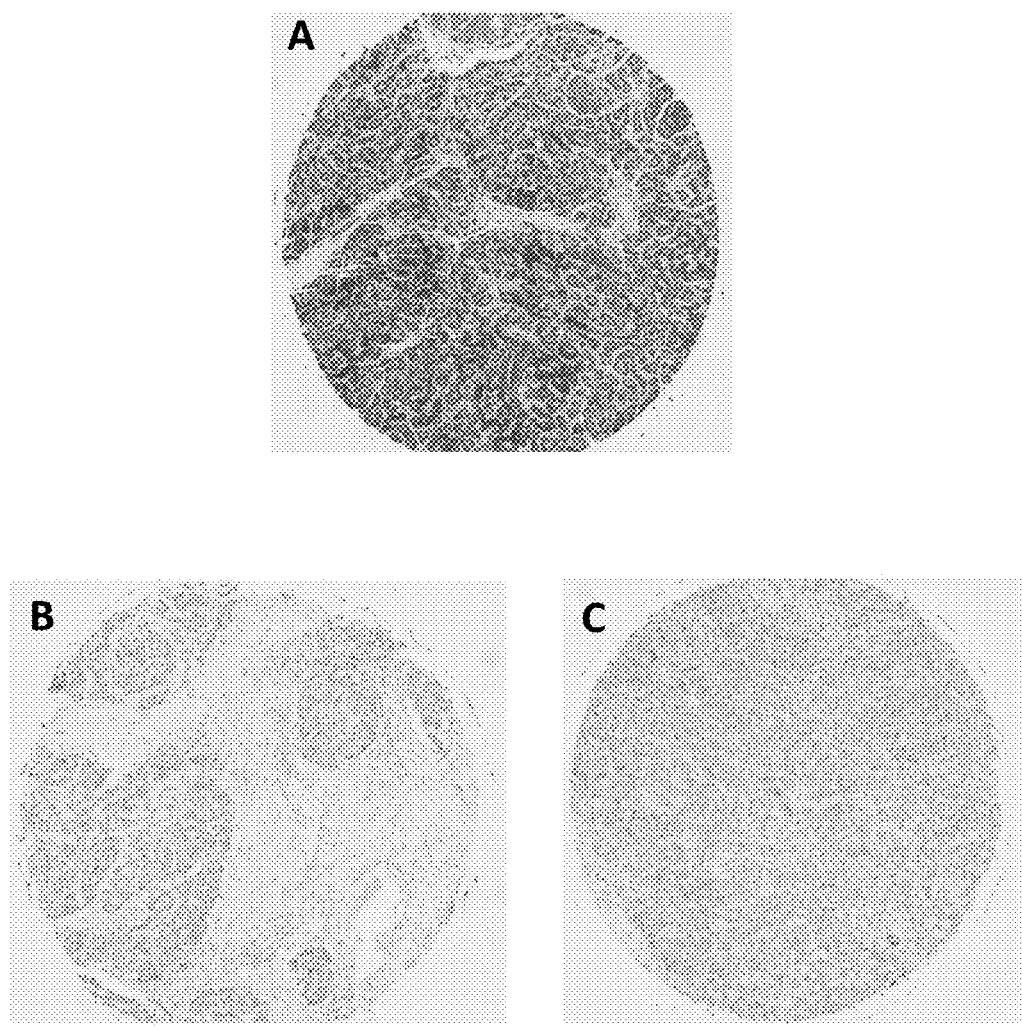
FIG. 6 shows the detection of argininosuccinate synthase expression in human hepatocellular carcinoma (HCC) microarrays by immunohistochemical staining with anti-argininosuccinate synthase monoclonal antibody.

Exemplary results are shown in FIGS. 4-6.

FIG. 4 shows the detection of argininosuccinate synthase expression in human cancer cell lines A431 (FIG. 4A) and SKMEL-3 (FIG. 4B) by immunohistochemical staining with anti-argininosuccinate synthase monoclonal antibody.

FIG. 5 shows the detection of argininosuccinate synthase expression in normal human tissues (FIG. 5A, kidney; FIG. 5B, skin; FIG. 5C, liver) by immunohistochemical staining with anti-argininosuccinate synthase monoclonal antibody.

FIG. 6 shows the detection of argininosuccinate synthase expression in human hepatocellular carcinoma (HCC) microarrays by immunohistochemical staining with anti-argininosuccinate synthase monoclonal antibody. FIG. 6A shows strong, positive staining for argininosuccinate synthase expression, and FIGS. 6B-6C show negative staining for argininosuccinate synthase expression.

These studies indicate that the performance characteristics of the anti-argininosuccinate synthase monoclonal antibody by immunohistochemistry (IHC) analysis are acceptable for clinical diagnostic applications in a variety of tissue types.

The invention claimed is:

1. An isolated antibody, or antigen-binding fragment thereof, which specifically binds to a human argininosuccinate synthase polypeptide and comprises a heavy chain variable region ($V_H$) sequence that comprises complementary determining region $V_H$CDR1, $V_H$CDR2, and $V_H$CDR3 sequences set forth respectively in SEQ ID NOs:7, 8, and 9, and a light chain variable region ($V_L$) sequence that comprises complementary determining region $V_L$CDR1, $V_L$CDR2, and $V_L$CDR3 sequences set forth respectively in SEQ ID NOs:10, 11, and 12.

2. The isolated antibody, or antigen-binding fragment thereof, of claim 1, where the $V_H$ sequence is at least 90% identical to SEQ ID NO:1.

3. The isolated antibody, or antigen-binding fragment thereof, of claim 1 or 2, where the $V_L$ sequence is at least 90% identical to SEQ ID NO:3.

4. The isolated antibody, or antigen-binding fragment thereof, of claim 1, where the $V_H$ sequence comprises SEQ ID NO:1 and the $V_L$ sequence comprises SEQ ID NO:3.

5. The isolated antibody, or antigen-binding fragment thereof, of claim 1, where the antibody is a whole antibody.

6. The isolated antibody, or antigen-binding fragment thereof, of claim 1, where the antibody is a monoclonal antibody.

7. The isolated antibody, or antigen-binding fragment thereof, of claim 1, which is selected from of a single chain antibody, a Fab or a Fab' fragment, F(ab')2 fragment, an ScFv, a univalent antibody lacking a hinge region, and a minibody.

8. The isolated antibody, or antigen-binding fragment thereof, of claim 1, where the antibody comprises a mouse or human IgG Fc domain, optionally a IgG1 or IgG2A Fc domain.

9. The isolated antibody, or antigen-binding fragment thereof, of claim 1, where the antibody is a mouse monoclonal antibody of subtype IgG1 or IgG2A.

10. The isolated antibody, or antigen-binding fragment thereof, of claim 1, comprising a covalently-attached detectable entity.

11. The isolated antibody, or antigen-binding fragment thereof, of claim 10, where the detectable entity is a fluorophore/fluorescent dye, an iodine-based label, a radioisotope, or a nanoparticle.

12. A composition, comprising an antibody of claim 1, and a suitable carrier.

13. A method of determining an amount of human argininosuccinate synthase polypeptide in a biological sample, comprising (a) obtaining or receiving a biological sample, optionally from a subject, (b) contacting the biological sample with an antibody, or antigen-binding fragment thereof, of claim 1, and (c) measuring the amount of the antibody, or antigen-binding fragment thereof, in the sample, where the amount of the antibody, or antigen-binding fragment thereof, determines the amount of the argininosuccinate synthase polypeptide in the sample.

14. A kit, comprising an isolated antibody of claim 1.

15. The kit of claim 14, comprising instructions for using the antibody according to a method of claim 13.

16. The kit of claim 14, further comprising materials and/or instructions for an immunohistochemistry (IHC) assay.

17. The kit of claim 14, further comprising materials and/or instructions for an enzyme-linked immunosorbent assay (ELISA), optionally where the antibody is attached to a solid substrate for performing an ELISA.

18. The kit of claim 14, comprising instructions for using the antibody to identify a subject for arginine deprivation therapy.

19. The kit of claim 17, where the arginine deprivation therapy is an arginine depletion agent, optionally ADI-PEG 20.

20. The kit of claim 14, further comprising at least one arginine depletion agent.

21. The kit of claim 20, where the arginine depletion agent is selected from an arginine deiminase (ADI) polypeptide, an arginase polypeptide, an arginine decarboxylase polypeptide, and an arginine kinase polypeptide.

22. The kit of claim 21, where the ADI polypeptide is ADI-PEG 20.

* * * * *

SEQUENCE LISTING

<160> NUMBER OF SEQ ID NOS: 23

<210> SEQ ID NO 1
<211> LENGTH: 113
<212> TYPE: PRT
<213> ORGANISM: Artificial Sequence
<220> FEATURE:
<223> OTHER INFORMATION: VH Chain determined by alignment of six
      productive sub-clones

<400> SEQUENCE: 1

Gln Ile Gln Leu Val Gln Ser Gly Pro Glu Leu Lys Lys Pro Gly Glu
1               5                   10                  15

Thr Val Lys Ile Ser Cys Lys Thr Ser Gly Tyr Thr Phe Thr Asp Tyr
                20                  25                  30

Ser Ile His Trp Val Lys Gln Ala Pro Gly Lys Gly Leu Thr Trp Met
            35                  40                  45

Gly Trp Ile Asn Thr Glu Thr Gly Glu Pro Thr Tyr Ala Asp Asp Phe
        50                  55                  60

Lys Gly Arg Phe Ala Leu Ser Leu Glu Thr Ser Ala Ser Thr Ala Tyr
65                  70                  75                  80

Leu Gln Leu Lys Asn Leu Arg Asn Glu Asp Thr Ala Thr Tyr Phe Cys
                85                  90                  95

Gly Ser Ser Tyr Ser Tyr Trp Gly Gln Gly Thr Leu Val Thr Val Ser
            100                 105                 110

Ser

<210> SEQ ID NO 2
<211> LENGTH: 339
<212> TYPE: DNA
<213> ORGANISM: Artificial Sequence
<220> FEATURE:
<223> OTHER INFORMATION: VH Chain determined by alignment of six
      productive sub-clones

<400> SEQUENCE: 2
cagatccagt tggtgcagtc tggacctgag ttgaagaagc tggagagac agtcaagatc      60 tcctgcaaga cttctggtta taccttcaca gactattcaa tacactgggt gaagcaggct    120
ccaggaaagg gtttaacgtg gatgggctgg ataaacactg agactggtga gccaacttat    180
gcagatgact tcaagggacg ctttgccctc tctttggaaa cctctgccag cactgcctat    240
ttgcagctca agaaacctcag aaatgaggac acggctacat atttctgtgg tagttcttat    300
tcttactggg gccaagggac tctggtcact gtctcttca                           339

<210> SEQ ID NO 3
<211> LENGTH: 112
<212> TYPE: PRT
<213> ORGANISM: Artificial Sequence
<220> FEATURE:
<223> OTHER INFORMATION: VL Chain determined by alignment of five
      productive sub-clones

<400> SEQUENCE: 3

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Glu Asn Ser
                20                  25                  30

Asn Gly Lys Thr Tyr Leu Asn Trp Phe Leu Gln Lys Pro Gly Gln Ser
            35                  40                  45

Pro Gln Leu Leu Ile Tyr Arg Val Ser Asn Arg Phe Ser Gly Val Pro
    50                  55                  60

Asp Arg Phe Ser Gly Ser Gly Ser Gly Thr Glu Phe Thr Leu Lys Ile
65                  70                  75                  80

Ser Arg Val Glu Ala Glu Asp Leu Gly Val Tyr Phe Cys Leu Gln Val
                85                  90                  95

Lys His Val Pro Trp Thr Phe Gly Gly Gly Thr Lys Leu Glu Ile Lys
            100                 105                 110

<210> SEQ ID NO 4
<211> LENGTH: 336
<212> TYPE: DNA
<213> ORGANISM: Artificial Sequence
<220> FEATURE:
<223> OTHER INFORMATION: VL Chain determined by alignment of five
      productive sub-clones

<400> SEQUENCE: 4
gatgttgtga tgacccaaac tccactctcc ctgcctgtca gtcttggaga tcaagcctcc      60
atctcttgca ggtctagtca gagccttgaa acagtaatg gaaagaccta tttgaactgg     120
ttcctcagaa aaccaggcca gtctccacag ctcctgatct acagggtttc caaccgattt     180
tctggggtcc cagacaggtt cagtggcagt ggatcaggga ctgaattcac actgaaaatc     240
agcagagtgg aggctgagga tttgggagtt tatttctgcc tccaagttaa acatgtcccg     300
tggacgttcg gtggaggcac caagctggaa atcaaa                               336

<210> SEQ ID NO 5
<211> LENGTH: 412
<212> TYPE: PRT
<213> ORGANISM: Homo sapiens

<400> SEQUENCE: 5

Met Ser Ser Lys Gly Ser Val Val Leu Ala Tyr Ser Gly Gly Leu Asp
1               5                   10                  15

Thr Ser Cys Ile Leu Val Trp Leu Lys Glu Gln Gly Tyr Asp Val Ile
            20                  25                  30

Ala Tyr Leu Ala Asn Ile Gly Gln Lys Glu Asp Phe Glu Glu Ala Arg
        35                  40                  45

Lys Lys Ala Leu Lys Leu Gly Ala Lys Lys Val Phe Ile Glu Asp Val
    50                  55                  60

Ser Arg Glu Phe Val Glu Glu Phe Ile Trp Pro Ala Ile Gln Ser Ser
65                  70                  75                  80

Ala Leu Tyr Glu Asp Arg Tyr Leu Leu Gly Thr Ser Leu Ala Arg Pro
                85                  90                  95

Cys Ile Ala Arg Lys Gln Val Glu Ile Ala Gln Arg Glu Gly Ala Lys
            100                 105                 110

Tyr Val Ser His Gly Ala Thr Gly Lys Gly Asn Asp Gln Val Arg Phe
        115                 120                 125

Glu Leu Ser Cys Tyr Ser Leu Ala Pro Gln Ile Lys Val Ile Ala Pro
    130                 135                 140

Trp Arg Met Pro Glu Phe Tyr Asn Arg Phe Lys Gly Arg Asn Asp Leu
145                 150                 155                 160

Met Glu Tyr Ala Lys Gln His Gly Ile Pro Ile Pro Val Thr Pro Lys
                165                 170                 175

Asn Pro Trp Ser Met Asp Glu Asn Leu Met His Ile Ser Tyr Glu Ala
            180                 185                 190

Gly Ile Leu Glu Asn Pro Lys Asn Gln Ala Pro Pro Gly Leu Tyr Thr
            195                 200                 205

Lys Thr Gln Asp Pro Ala Lys Ala Pro Asn Thr Pro Asp Ile Leu Glu
210                 215                 220

Ile Glu Phe Lys Lys Gly Val Pro Val Lys Val Thr Asn Val Lys Asp
225                 230                 235                 240

Gly Thr Thr His Gln Thr Ser Leu Glu Leu Phe Met Tyr Leu Asn Glu
            245                 250                 255

Val Ala Gly Lys His Gly Val Gly Arg Ile Asp Ile Val Glu Asn Arg
            260                 265                 270

Phe Ile Gly Met Lys Ser Arg Gly Ile Tyr Glu Thr Pro Ala Gly Thr
            275                 280                 285

Ile Leu Tyr His Ala His Leu Asp Ile Glu Ala Phe Thr Met Asp Arg
            290                 295                 300

Glu Val Arg Lys Ile Lys Gln Gly Leu Gly Leu Lys Phe Ala Glu Leu
305                 310                 315                 320

Val Tyr Thr Gly Phe Trp His Ser Pro Glu Cys Glu Phe Val Arg His
            325                 330                 335

Cys Ile Ala Lys Ser Gln Glu Arg Val Glu Gly Lys Val Gln Val Ser
            340                 345                 350

Val Leu Lys Gly Gln Val Tyr Ile Leu Gly Arg Glu Ser Pro Leu Ser
            355                 360                 365

Leu Tyr Asn Glu Glu Leu Val Ser Met Asn Val Gln Gly Asp Tyr Glu
            370                 375                 380

Pro Thr Asp Ala Thr Gly Phe Ile Asn Ile Asn Ser Leu Arg Leu Lys
385                 390                 395                 400

Glu Tyr His Arg Leu Gln Ser Lys Val Thr Ala Lys
            405                 410

<210> SEQ ID NO 6
<211> LENGTH: 409
<212> TYPE: PRT
<213> ORGANISM: Mycoplasma hominis

<400> SEQUENCE: 6

Met Ser Val Phe Asp Ser Lys Phe Asn Gly Ile His Val Tyr Ser Glu
1               5                   10                  15

Ile Gly Glu Leu Glu Thr Val Leu Val His Glu Pro Gly Arg Glu Ile
            20                  25                  30

Asp Tyr Ile Thr Pro Ala Arg Leu Asp Glu Leu Leu Phe Ser Ala Ile
            35                  40                  45

Leu Glu Ser His Asp Ala Arg Lys Glu His Gln Ser Phe Val Lys Ile
        50                  55                  60

Met Lys Asp Arg Gly Ile Asn Val Val Glu Leu Thr Asp Leu Val Ala
65                  70                  75                  80

Glu Thr Tyr Asp Leu Ala Ser Lys Ala Ala Lys Glu Glu Phe Ile Glu
            85                  90                  95

Thr Phe Leu Glu Glu Thr Val Pro Val Leu Thr Glu Ala Asn Lys Lys
            100                 105                 110

Ala Val Arg Ala Phe Leu Leu Ser Lys Pro Thr His Glu Met Val Glu
            115                 120                 125

Phe Met Met Ser Gly Ile Thr Lys Tyr Glu Leu Gly Val Glu Ser Glu
            130                 135                 140

Asn Glu Leu Ile Val Asp Pro Met Pro Asn Leu Tyr Phe Thr Arg Asp
145                 150                 155                 160

-continued

Pro Phe Ala Ser Val Gly Asn Gly Val Thr Ile His Phe Met Arg Tyr
                165                 170                 175

Ile Val Arg Arg Glu Thr Leu Phe Ala Arg Phe Val Phe Arg Asn
            180                 185                 190

His Pro Lys Leu Val Lys Thr Pro Trp Tyr Tyr Asp Pro Ala Met Lys
        195                 200                 205

Met Pro Ile Glu Gly Gly Asp Val Phe Ile Tyr Asn Asn Glu Thr Leu
    210                 215                 220

Val Val Gly Val Ser Glu Arg Thr Asp Leu Asp Thr Ile Thr Leu Leu
225                 230                 235                 240

Ala Lys Asn Ile Lys Ala Asn Lys Glu Val Glu Phe Lys Arg Ile Val
                245                 250                 255

Ala Ile Asn Val Pro Lys Trp Thr Asn Leu Met His Leu Asp Thr Trp
            260                 265                 270

Leu Thr Met Leu Asp Lys Asn Lys Phe Leu Tyr Ser Pro Ile Ala Asn
        275                 280                 285

Asp Val Phe Lys Phe Trp Asp Tyr Asp Leu Val Asn Gly Gly Ala Glu
    290                 295                 300

Pro Gln Pro Gln Leu Asn Gly Leu Pro Leu Asp Lys Leu Leu Ala Ser
305                 310                 315                 320

Ile Ile Asn Lys Glu Pro Val Leu Ile Pro Ile Gly Gly Ala Gly Ala
                325                 330                 335

Thr Glu Met Glu Ile Ala Arg Glu Thr Asn Phe Asp Gly Thr Asn Tyr
            340                 345                 350

Leu Ala Ile Lys Pro Gly Leu Val Ile Gly Tyr Asp Arg Asn Glu Lys
        355                 360                 365

Thr Asn Ala Ala Leu Lys Ala Ala Gly Ile Thr Val Leu Pro Phe His
    370                 375                 380

Gly Asn Gln Leu Ser Leu Gly Met Gly Asn Ala Arg Cys Met Ser Met
385                 390                 395                 400

Pro Leu Ser Arg Lys Asp Val Lys Trp
                405

<210> SEQ ID NO 7
<211> LENGTH: 8
<212> TYPE: PRT
<213> ORGANISM: Artificial Sequence
<220> FEATURE:
<223> OTHER INFORMATION: VH CDR1 determined by alignment of six
      productive sub-clones

<400> SEQUENCE: 7

Gly Tyr Thr Phe Thr Asp Tyr Ser
1               5

<210> SEQ ID NO 8
<211> LENGTH: 8
<212> TYPE: PRT
<213> ORGANISM: Artificial Sequence
<220> FEATURE:
<223> OTHER INFORMATION: VH CDR2 determined by alignment of six
      productive sub-clones

<400> SEQUENCE: 8

Ile Asn Thr Glu Thr Gly Glu Pro
1               5

<210> SEQ ID NO 9

```
<211> LENGTH: 6
<212> TYPE: PRT
<213> ORGANISM: Artificial Sequence
<220> FEATURE:
<223> OTHER INFORMATION: VH CDR3 determined by alignment of six
      productive sub-clones

<400> SEQUENCE: 9

Gly Ser Ser Tyr Ser Tyr
1               5

<210> SEQ ID NO 10
<211> LENGTH: 11
<212> TYPE: PRT
<213> ORGANISM: Artificial Sequence
<220> FEATURE:
<223> OTHER INFORMATION: VL CDR1 determined by alignment of five
      productive sub-clones

<400> SEQUENCE: 10

Gln Ser Leu Glu Asn Ser Asn Gly Lys Thr Tyr
1               5                   10

<210> SEQ ID NO 11
<211> LENGTH: 3
<212> TYPE: PRT
<213> ORGANISM: Artificial Sequence
<220> FEATURE:
<223> OTHER INFORMATION: VL CDR2 determined by alignment of five
      productive sub-clones

<400> SEQUENCE: 11

Arg Val Ser
1

<210> SEQ ID NO 12
<211> LENGTH: 9
<212> TYPE: PRT
<213> ORGANISM: Artificial Sequence
<220> FEATURE:
<223> OTHER INFORMATION: VL CDR3 determined by alignment of five
      productive sub-clones

<400> SEQUENCE: 12

Leu Gln Val Lys His Val Pro Trp Thr
1               5

<210> SEQ ID NO 13
<211> LENGTH: 113
<212> TYPE: PRT
<213> ORGANISM: Artificial Sequence
<220> FEATURE:
<223> OTHER INFORMATION: VH sequence from productive sub-clone (6-H6) of
      hybridoma antibody clone

<400> SEQUENCE: 13

Gln Ile Gln Leu Val Gln Ser Gly Pro Glu Leu Lys Lys Pro Gly Glu
1               5                   10                  15

Thr Val Lys Ile Ser Cys Lys Thr Ser Gly Tyr Thr Phe Thr Asp Tyr
            20                  25                  30

Ser Ile His Trp Val Lys Gln Ala Pro Gly Lys Gly Leu Thr Trp Met
        35                  40                  45

Gly Trp Ile Asn Thr Glu Thr Gly Glu Pro Tyr Ala Asp Asp Phe
    50                  55                  60

Lys Gly Arg Phe Ala Leu Ser Leu Glu Thr Ser Ala Ser Thr Ala Tyr
65                  70                  75                  80
```

```
Leu Gln Leu Lys Asn Leu Arg Asn Glu Asp Thr Ala Thr Tyr Phe Cys
                85                  90                  95

Gly Ser Ser Tyr Ser Tyr Trp Gly Gln Gly Thr Leu Val Thr Val Ser
            100                 105                 110

Ser

<210> SEQ ID NO 14
<211> LENGTH: 113
<212> TYPE: PRT
<213> ORGANISM: Artificial Sequence
<220> FEATURE:
<223> OTHER INFORMATION: VH sequence from productive sub-clone (6-C5) of
      hybridoma antibody clone

<400> SEQUENCE: 14

Gln Ile Gln Leu Val Gln Ser Gly Pro Glu Ser Lys Lys Pro Gly Glu
1               5                   10                  15

Thr Val Lys Ile Ser Cys Lys Thr Ser Gly Tyr Thr Phe Thr Asp Tyr
            20                  25                  30

Ser Ile His Trp Val Lys Gln Ala Pro Gly Lys Gly Leu Thr Trp Met
        35                  40                  45

Gly Trp Ile Asn Thr Glu Thr Gly Glu Pro Thr Tyr Ala Asp Asp Phe
    50                  55                  60

Lys Gly Arg Phe Ala Leu Ser Leu Glu Thr Ser Ala Ser Thr Ala Tyr
65                  70                  75                  80

Leu Gln Leu Lys Asn Leu Arg Asn Glu Asp Thr Ala Thr Tyr Phe Cys
                85                  90                  95

Gly Ser Ser Tyr Ser Tyr Trp Gly Gln Gly Thr Leu Val Thr Val Ser
            100                 105                 110

Ser

<210> SEQ ID NO 15
<211> LENGTH: 113
<212> TYPE: PRT
<213> ORGANISM: Artificial Sequence
<220> FEATURE:
<223> OTHER INFORMATION: VH sequence from productive sub-clone (6-C1) of
      hybridoma antibody clone

<400> SEQUENCE: 15

Gln Ile Gln Leu Val Gln Ser Gly Pro Glu Leu Lys Lys Pro Gly Glu
1               5                   10                  15

Thr Val Lys Ile Pro Cys Lys Thr Ser Gly Tyr Thr Phe Thr Asp Tyr
            20                  25                  30

Ser Ile His Trp Val Lys Gln Ala Pro Gly Lys Gly Leu Thr Trp Met
        35                  40                  45

Gly Trp Ile Asn Thr Glu Thr Gly Glu Pro Thr Tyr Ala Asp Asp Phe
    50                  55                  60

Lys Gly Arg Phe Ala Leu Ser Leu Glu Thr Ser Ala Ser Thr Ala Tyr
65                  70                  75                  80

Leu Gln Leu Lys Asn Leu Arg Asn Glu Asp Thr Ala Thr Tyr Phe Cys
                85                  90                  95

Gly Ser Ser Tyr Ser Tyr Trp Gly Gln Gly Thr Leu Val Thr Val Ser
            100                 105                 110

Ser

<210> SEQ ID NO 16
```

-continued

```
<211> LENGTH: 113
<212> TYPE: PRT
<213> ORGANISM: Artificial Sequence
<220> FEATURE:
<223> OTHER INFORMATION: VH sequence from productive sub-clone (6-L7) of
      hybridoma antibody clone

<400> SEQUENCE: 16

Gln Ile Gln Leu Val Gln Ser Gly Pro Glu Leu Lys Glu Pro Gly Glu
1               5                   10                  15

Thr Val Lys Ile Ser Cys Lys Thr Ser Gly Tyr Thr Phe Thr Asp Tyr
            20                  25                  30

Ser Ile His Trp Val Lys Gln Ala Pro Gly Lys Gly Leu Thr Trp Met
        35                  40                  45

Gly Trp Ile Asn Thr Glu Thr Gly Glu Pro Thr Tyr Ala Asp Asp Phe
    50                  55                  60

Lys Gly Arg Phe Ala Leu Ser Leu Glu Thr Ser Ala Ser Thr Ala Tyr
65                  70                  75                  80

Leu Gln Leu Lys Asn Leu Arg Asn Glu Asp Thr Ala Thr Tyr Phe Cys
                85                  90                  95

Gly Ser Ser Tyr Ser Tyr Trp Gly Gln Gly Thr Leu Val Thr Val Ser
            100                 105                 110

Ser

<210> SEQ ID NO 17
<211> LENGTH: 113
<212> TYPE: PRT
<213> ORGANISM: Artificial Sequence
<220> FEATURE:
<223> OTHER INFORMATION: VH sequence from productive sub-clone (6-A5) of
      hybridoma antibody clone

<400> SEQUENCE: 17

Gln Ile Gln Leu Val Gln Ser Gly Pro Glu Leu Lys Lys Pro Gly Glu
1               5                   10                  15

Thr Val Lys Ile Ser Cys Lys Thr Ser Gly Tyr Thr Phe Thr Asp Tyr
            20                  25                  30

Ser Ile His Trp Val Lys Gln Ala Pro Gly Lys Gly Leu Thr Trp Met
        35                  40                  45

Gly Trp Ile Asn Thr Glu Thr Gly Glu Pro Thr Tyr Ala Asp Asp Phe
    50                  55                  60

Lys Gly Arg Phe Ala Leu Ser Leu Glu Thr Ser Ala Ser Thr Ala Tyr
65                  70                  75                  80

Leu Gln Leu Lys Asn Leu Arg Asn Glu Asp Thr Ala Thr Tyr Phe Cys
                85                  90                  95

Gly Ser Ser Tyr Ser Tyr Trp Gly Gln Gly Thr Leu Val Thr Val Ser
            100                 105                 110

Ser

<210> SEQ ID NO 18
<211> LENGTH: 113
<212> TYPE: PRT
<213> ORGANISM: Artificial Sequence
<220> FEATURE:
<223> OTHER INFORMATION: VH sequence from productive sub-clone (6-D6) of
      hybridoma antibody clone

<400> SEQUENCE: 18

Gln Ile Gln Leu Val Gln Ser Gly Pro Glu Leu Lys Lys Pro Gly Glu
1               5                   10                  15
```

```
Thr Val Lys Ile Ser Cys Lys Thr Gly Tyr Thr Phe Thr Asp Tyr
            20                  25                  30

Ser Ile His Trp Val Lys Gln Ala Pro Gly Lys Gly Leu Thr Trp Met
        35                  40                  45

Gly Trp Ile Asn Thr Glu Thr Gly Glu Pro Thr Tyr Ala Asp Asp Phe
 50                  55                  60

Lys Gly Arg Phe Ala Leu Ser Leu Glu Thr Ser Ala Ser Thr Ala Tyr
 65                  70                  75                  80

Leu Gln Leu Lys Asn Leu Arg Asn Glu Asp Thr Ala Thr Tyr Phe Cys
                85                  90                  95

Gly Ser Ser Tyr Ser Tyr Trp Gly Gln Gly Thr Leu Val Thr Val Ser
            100                 105                 110

Ser

<210> SEQ ID NO 19
<211> LENGTH: 112
<212> TYPE: PRT
<213> ORGANISM: Artificial Sequence
<220> FEATURE:
<223> OTHER INFORMATION: VL sequence from productive sub-clone (4-5) of
      hybridoma antibody clone

<400> SEQUENCE: 19

Asp Val Val Met Thr Gln Thr Pro Leu Ser Leu Pro Val Ser Leu Gly
 1               5                  10                  15

Asp Gln Ala Ser Ile Ser Cys Arg Ser Ser Gln Ser Leu Glu Asn Ser
            20                  25                  30

Asn Gly Lys Thr Tyr Leu Asn Trp Phe Leu Gln Lys Pro Gly Gln Ser
        35                  40                  45

Pro Gln Leu Leu Ile Tyr Arg Val Ser Asn Arg Phe Ser Gly Val Pro
 50                  55                  60

Asp Arg Phe Ser Gly Ser Gly Ser Gly Thr Glu Phe Thr Leu Lys Ile
 65                  70                  75                  80

Ser Arg Val Glu Ala Glu Asp Leu Gly Val Tyr Phe Cys Leu Gln Val
                85                  90                  95

Lys His Val Pro Trp Thr Phe Gly Gly Gly Thr Lys Leu Glu Ile Lys
            100                 105                 110

<210> SEQ ID NO 20
<211> LENGTH: 112
<212> TYPE: PRT
<213> ORGANISM: Artificial Sequence
<220> FEATURE:
<223> OTHER INFORMATION: VL sequence from productive sub-clone (7-2) of
      hybridoma antibody clone

<400> SEQUENCE: 20

Asp Val Val Met Thr Gln Thr Pro Leu Ser Leu Pro Val Ser Leu Gly
 1               5                  10                  15

Asp Gln Ala Ser Ile Ser Cys Arg Ser Ser Gln Ser Leu Glu Asn Ser
            20                  25                  30

Asn Gly Lys Thr Tyr Leu Asn Trp Phe Leu Gln Lys Pro Gly Gln Ser
        35                  40                  45

Pro Gln Leu Leu Ile Tyr Arg Val Ser Asn Arg Phe Ser Gly Val Pro
 50                  55                  60

Asp Arg Phe Ser Gly Ser Gly Ser Gly Thr Glu Phe Thr Leu Lys Ile
 65                  70                  75                  80
```

-continued

Ser Arg Val Glu Ala Glu Asp Leu Gly Val Tyr Phe Cys Leu Gln Val
                85                  90                  95

Lys His Val Pro Trp Thr Phe Gly Gly Gly Thr Lys Leu Glu Ile Lys
            100                 105                 110

<210> SEQ ID NO 21
<211> LENGTH: 112
<212> TYPE: PRT
<213> ORGANISM: Artificial Sequence
<220> FEATURE:
<223> OTHER INFORMATION: VL sequence from productive sub-clone (7-8) of
      hybridoma antibody clone

<400> SEQUENCE: 21

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Glu Asn Ser
            20                  25                  30

Asn Gly Lys Thr Tyr Leu Asn Trp Phe Leu Gln Lys Pro Gly Gln Ser
        35                  40                  45

Pro Gln Leu Leu Ile Tyr Arg Val Ser Asn Arg Phe Ser Gly Val Pro
    50                  55                  60

Asp Arg Phe Ser Gly Ser Gly Ser Gly Thr Glu Phe Thr Leu Lys Ile
65                  70                  75                  80

Ser Arg Val Glu Ala Glu Asp Leu Gly Val Tyr Phe Cys Leu Gln Val
                85                  90                  95

Lys His Val Pro Trp Thr Phe Gly Gly Gly Thr Lys Leu Glu Ile Lys
            100                 105                 110

<210> SEQ ID NO 22
<211> LENGTH: 112
<212> TYPE: PRT
<213> ORGANISM: Artificial Sequence
<220> FEATURE:
<223> OTHER INFORMATION: VL sequence from productive sub-clone (7-12) of
      hybridoma antibody clone

<400> SEQUENCE: 22

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Glu Asn Ser
            20                  25                  30

Asn Gly Lys Thr Tyr Leu Asn Trp Phe Leu Gln Lys Pro Gly Gln Ser
        35                  40                  45

Pro Gln Leu Leu Ile Tyr Arg Val Pro Asn Arg Phe Ser Gly Val Pro
    50                  55                  60

Asp Arg Phe Ser Gly Ser Gly Ser Gly Thr Glu Phe Thr Leu Lys Ile
65                  70                  75                  80

Ser Arg Val Glu Ala Glu Asp Leu Gly Val Tyr Phe Cys Leu Gln Val
                85                  90                  95

Lys His Val Pro Trp Thr Phe Gly Gly Gly Thr Lys Leu Glu Ile Lys
            100                 105                 110

<210> SEQ ID NO 23
<211> LENGTH: 112
<212> TYPE: PRT
<213> ORGANISM: Artificial Sequence
<220> FEATURE:
<223> OTHER INFORMATION: VL sequence from productive sub-clone (7-4) of
      hybridoma antibody clone

```
<400> SEQUENCE: 23

Asp Val Val Met Thr Gln Thr Pro Leu Ser Leu Pro Val Ser Leu Gly
1               5                   10                  15

Asp Gln Ala Ser Thr Ser Cys Arg Ser Ser Gln Ser Leu Glu Asn Ser
                20                  25                  30

Asn Gly Lys Thr Tyr Leu Asn Trp Phe Leu Gln Lys Pro Gly Gln Ser
            35                  40                  45

Pro Gln Leu Leu Ile Tyr Arg Val Ser Asn Arg Phe Ser Gly Val Pro
        50                  55                  60

Asp Arg Phe Ser Gly Ser Gly Ser Gly Thr Glu Phe Thr Leu Lys Ile
65                  70                  75                  80

Ser Arg Val Glu Ala Glu Asp Leu Gly Val Tyr Phe Cys Leu Gln Val
                85                  90                  95

Lys His Val Pro Trp Thr Phe Gly Gly Gly Thr Lys Leu Glu Ile Lys
                100                 105                 110
```